United States Patent
Ochsenbein et al.

(10) Patent No.: US 9,526,757 B2
(45) Date of Patent: Dec. 27, 2016

(54) PEPTIDES THAT INHIBIT THE INTERACTION BETWEEN ASF1 AND HISTONES, AND USE THEREOF

(71) Applicant: COMMISSARIAT A L'ENERGIE ATOMIQUE ET AUX ENERGIES ALTERNATIVES, Paris (FR)

(72) Inventors: Francoise Ochsenbein, Gif sur Yvette (FR); Raphael Guerois, Gif sur Yvette (FR); Albane Gaubert, Saint Cloud (FR); Regis Courbeyrette, Massy (FR)

(73) Assignees: COMMISSARIAT A L'ENERGIE ATOMIQUE ET AUX ENERGIES ALTERNATIVES, Paris (FR); UNIVERSITE PIERRE ET MARIE CURIE (PARIS VI), Paris (FR)

( * ) Notice: Subject to any disclaimer, the term of this patent is extended or adjusted under 35 U.S.C. 154(b) by 0 days.

(21) Appl. No.: 14/358,875

(22) PCT Filed: Nov. 16, 2012

(86) PCT No.: PCT/FR2012/052641
§ 371 (c)(1),
(2) Date: May 16, 2014

(87) PCT Pub. No.: WO2013/072636
PCT Pub. Date: May 23, 2013

(65) Prior Publication Data
US 2015/0025016 A1    Jan. 22, 2015

(30) Foreign Application Priority Data
Nov. 18, 2011  (FR) ...................... 11 60536

(51) Int. Cl.
| | | |
|---|---|---|
| *A61K 38/16* | (2006.01) |
| *A61K 38/00* | (2006.01) |
| *A61K 38/10* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/03* | (2006.01) |
| *C07K 14/00* | (2006.01) |
| *C07K 14/47* | (2006.01) |

(52) U.S. Cl.
CPC .............. *A61K 38/16* (2013.01); *A61K 38/03* (2013.01); *C07K 14/00* (2013.01); *C07K 14/001* (2013.01); *C07K 14/47* (2013.01); *A61K 38/00* (2013.01)

(58) Field of Classification Search
None
See application file for complete search history.

(56) References Cited

PUBLICATIONS

NCBI Database, GenBank Accession No. CAE07819, 1 page (first available 2003).*
Ter-Avetisyan et al., J. Biol. Chem. 284:3370-3378 (2009).*
Antczak, A. et al. "Structure of the yeast histone H3-ASFI interaction: implications for chaperone mechanism, species-specific interactions, and epigenetics" *BMC Structural Biology*, Dec. 13, 2006, pp. 1-12, vol. 6, No. 1.
Groth, A. et al. "Human Asf1 Regulates the Flow of S Phase Histones during Replicational Stress" *Molecular Cell*, Jan. 21, 2005, pp. 301-311, vol. 17, No. 2.
De Benedetti, A. "Tousled kinase TLKIB counteracts the effect of Asf1 in inhibition of histone H3-H4 tetramer formation" *BMC Structural Biology*, Jul. 8, 2009, pp. 1-5, vol. 2, No. 128.

* cited by examiner

*Primary Examiner* — Hasan Ahmed
*Assistant Examiner* — Thea D'Ambrosio
(74) *Attorney, Agent, or Firm* — Saliwanchik, Lloyd & Eisenschenk

(57) ABSTRACT

The present invention relates to peptides capable of inhibiting the formation of the complex between the Asf1 histone chaperone and histones H3-H4, and to the use thereof as a drug, particularly for treating cancer.

11 Claims, 15 Drawing Sheets

PEPTIDES THAT INHIBIT THE INTERACTION BETWEEN ASF1 AND HISTONES, AND USE THEREOF

CROSS-REFERENCE TO RELATED APPLICATION

This application is the U.S. national stage application of International Patent Application No. PCT/FR2012/052641, filed Nov. 16, 2012.

The Sequence Listing for this application is labeled "Seq-List-replace.txt" which was created on Sep. 8, 2014 and is 47 KB. The entire contents of the sequence listing is incorporated herein by reference in its entirety.

The present invention relates to a new class of molecules of therapeutic interest, particularly in the field of oncology.

To protect their genomes, cells have developed several strategies. Firstly, DNA is protected from oxidative damage by a compact protein structure called chromatin. Secondly, DNA repair and signaling machinery exists that deals with DNA damage to restore an intact genome. The histone chaperone Asf1 (Anti-Silencing Factor 1) is located at the crossroads of DNA repair and the molecular checkpoint machinery ensuring the maintenance of chromatin.

Asf1 participates in the deposition of histones H3/H4 onto DNA during numerous cellular processes. Deletion of Asf1 in different species (yeast, human, chicken, *Drosophila*) slows proliferation, sensitizes cells to genotoxic agents used in conventional chemotherapy and prevents the establishment of specific epigenetic markers, thereby revealing the crucial role of Asf1 in chromatin assembly, cellular responses to DNA damage and maintenance of epigenetic information.

Very recent studies have shown that in human cells, inhibition of Asf1 by siRNA causes arrest of cells in S phase. On the other hand, overexpression of the Asf1b isoform in malignant cells is a particularly powerful prognostic marker for the severity of breast tumors (Corpet et al, 2011, Embo J. 30(3): 480-93). The latter study demonstrates, for the first time, the involvement of Asf1 histone chaperone in the development of cancers.

Structural and functional analysis of Asf1 histone chaperone has shown that the interaction between Asf1 and histones is required for all of its functions (Mousson, et al. 2005, PNAS USA, 2005. 102(17): 5975-5980; Agez et al. 2007, Structure, 2007. 15(2): 191-199; and Galvani et al. 2008, Molecular and Cellular Biology, 2008. 28(11): 3672-3685).

The interaction between Asf1 and histones is therefore an attractive target for the development of new anticancer agents. Molecules capable of inhibiting this interaction will potentially have anticancer properties not only by disruption of proliferation, but also of epigenetic information and by sensitization of cells to conventional anticancer agents.

Inhibition of Asf1 by the siRNA method is effective in cell culture, but at present there are some difficulties to implementing it as a medicament in vivo.

The inventors provide through the present invention an alternative strategy based on a peptide approach. A classical strategy for designing peptide inhibitors of the interaction of two proteins, particularly in a complex, consists of the development of a peptide interacting with one of the partners of the complex.

The inventors have chosen, in the present invention, to target multiple partners interacting with Asf1, in particular both histone H3 and histone H4. Thus, through the present invention, the inventors provide peptides that inhibit the formation of the complex between Asf1 and histones H3-H4.

An advantage of the present invention comes from the fact that the target does not correspond to an enzyme or a receptor, as is usually the case, but to a protein-protein interaction. Indeed, it is a matter of inhibiting a transient and labile interaction between the assembly chaperone, Asf1, and a subunit of the target complex, the nucleosome. Thus, a peptide acting on a transient interaction will be more effective than when the peptide must inhibit a stable final complex. This peptide strategy has the additional advantage of high specificity, thus preventing side effects. Moreover, the target complex, which is vital, can still form spontaneously in the absence of chaperone protein. One can therefore modulate the amount of complex formed and therefore the magnitude of the action of the molecules.

The present invention therefore relates to a peptide molecule, capable of inhibiting the formation of the complex between Asf1 and histones H3-H4, comprising or consisting of the elements E1-B-E2 (arranged in the N-terminal to C-terminal direction). E1 and E2 correspond to the peptide targeting the binding region of histone H3 and that of histone H4, respectively, and B is the peptide loop connecting these two elements. The elements E1-B-E2 are as defined below:

a) E1 is a peptide of formula (I)

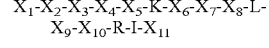

$X_1\text{-}X_2\text{-}X_3\text{-}X_4\text{-}X_5\text{-}K\text{-}X_6\text{-}X_7\text{-}X_8\text{-}L\text{-}X_9\text{-}X_{10}\text{-}R\text{-}I\text{-}X_{11}$      (I) (SEQ ID NO: 2)

wherein a1) or (SEQ ID NO: 1)

$X_1$ and $X_2$ are absent;

$X_3$ is a hydrophobic amino acid or R, preferably selected from the group consisting of A, C, V, P, L, I, M, F, W, R and Y, and even more preferably from the group consisting of A, C, V, P, L, I, M, F, W and Y;

$X_4$ is an amino acid selected from the group consisting of T, S, P, D, M and N, preferably from the group consisting of T, S, P, D and N;

$X_5$ is any amino acid, preferably selected from the natural amino acids (A, R, D, N, C, G, Q, E, H, I, L, K, M, F, P, S, T, V, W and Y);

$X_6$ is an amino acid selected from the group consisting of Q, E, L, M, A, D and W, preferably from the group consisting of Q, E, L, M, A and W;

$X_7$, $X_8$ and $X_9$, independently of each other, are any amino acid, preferably selected from the natural amino acids (A, R, D, N, C, G, Q, E, H, I, L, K, M, F, P, S, T, V, W and Y), provided that at least two of the residues $X_7$, $X_8$ and $X_9$ are an amino acid favorable to an alpha helix secondary structure, preferably selected from the group consisting of A, R, D, N, C, G, Q, E, H, L, K, M, F, S, W and Y; and $X_{10}$ and $X_{11}$, independently of each other, are any amino acid, preferably selected from the natural amino acids (A, R, D, N, C, G, Q, E, H, I, L, K, M, F, P, S, T, V, W and Y);

a2) or (SEQ ID NO: 2)

$X_1$ is absent or is any amino acid, preferably selected from the natural amino acids (A, R, D, N, C, G, Q, E, H, I, L, K, M, F, P, S, T, V, W and Y);

$X_2$ is absent or is any amino acid, preferably selected from the natural amino acids (A, R, D, N, C, G, Q, E, H, I, L, K, M, F, P, S, T, V, W and Y);

$X_3$ is an amino acid selected from the group consisting of T, S, P, D and N;

$X_4$ and $X_5$, independently of each other, are an amino acid favorable to an alpha helix secondary structure, preferably selected from the group consisting of A, R, D, N, C, G, Q, E, H, L, K, M, F, S, W and Y;

$X_6$ is an amino acid selected from the group consisting of Q, E, L, M, A, D and W, preferably from the group consisting of Q, E, L, M, A and W;

$X_7$, $X_8$ and $X_9$, independently of each other, are any amino acid, preferably selected from the natural amino acids (A, R, D, N, C, G, Q, E, H, I, L, K, M, F, P, S, T, V, W and Y), provided that at least two of the residues $X_7$, $X_8$ and $X_9$ are an amino acid favorable to an alpha helix secondary structure, preferably selected from the group consisting of A, R, D, N, C, G, Q, E, H, L, K, M, F, S, W and Y; and $X_{10}$ and $X_{11}$, independently of each other, are any amino acid, preferably selected from the natural amino acids (A, R, D, N, C, G, Q, E, H, I, L, K, M, F, P, S, T, V, W and Y);

b) B is a peptide of formula (II)

G-$X_{12}$-G-$X_{13}$-$X_{14}$      (II) (SEQ ID NO: 3)

wherein $X_{12}$ is any amino acid, preferably selected from the natural amino acids (A, R, D, N, C, G, Q, E, H, I, L, K, M, F, P, S, T, V, W and Y);

$X_{13}$ is absent or selected from the amino acids G, A and S;

$X_{14}$ is absent or is any amino acid, preferably selected from the natural amino acids (A, R, D, N, C, G, Q, E, H, I, L, K, M, F, P, S, T, V, W and Y);

and c) E2 is a peptide of formula (III)

$X_{15}$-$X_{16}$-$X_{17}$-$X_{18}$-G-$X_{19}$-$X_{20}$      (III) (SEQ ID NO: 4)

wherein $X_{15}$ is any amino acid, preferably selected from the natural amino acids (A, R, D, N, C, G, Q, E, H, I, L, K, M, F, P, S, T, V, W and Y), preferably from A, T, V, I and R, even more preferably it is R or V;

$X_{16}$ is T or V;

$X_{17}$ is any amino acid, preferably selected from the natural amino acids (A, R, D, N, C, G, Q, E, H, I, L, K, M, F, P, S, T, V, W and Y);

$X_{18}$ is any non-positively charged amino acid, preferably selected from the group consisting of A, D, N, C, G, Q, E, H, I, L, M, F, P, S, T, V, W and Y;

$X_{19}$ is a hydrophobic amino acid, preferably selected from the group consisting of A, C, V, P, L, I, M, F, W and Y; and $X_{20}$ is absent or is any amino acid, preferably selected from the natural amino acids (A, R, D, N, C, G, Q, E, H, I, L, K, M, F, P, S, T, V, W and Y).

Preferably, the peptide molecule comprises the elements E1-B-E2, in which either:

$X_1$ and $X_2$ are absent;

$X_3$ is a hydrophobic amino acid selected from the group consisting of A, C, V, P, L, I, M, F, W and Y;

$X_4$ is an amino acid selected from the group consisting of T, S, P, D and N;

$X_5$ is any amino acid, preferably selected from the natural amino acids (A, R, D, N, C, G, Q, E, H, I, L, K, M, F, P, S, T, V, W and Y);

$X_6$ is an amino acid selected from the group consisting of Q, E, L, M, A, and W;

$X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y; and $X_{10}$ and $X_{11}$, independently of each other, are any amino acid, preferably selected from the natural amino acids (A, R, D, N, C, G, Q, E, H, I, L, K, M, F, P, S, T, V, W and Y);

or $X_1$, $X_2$, $X_{10}$ and $X_{11}$, independently of each other, are any amino acid, preferably selected from the natural amino acids (A, R, D, N, C, G, Q, E, H, I, L, K, M, F, P, S, T, V, W and Y);

$X_4$ and $X_5$, independently of each other, are an amino acid favorable to an alpha helix secondary structure, preferably selected from the group consisting of A, R, D, N, C, G, Q, E, H, L, K, M, F, S, W and Y;

$X_3$ is an amino acid selected from the group consisting of T, S, P, D and N;

$X_6$ is an amino acid selected from the group consisting of Q, E, L, M, A, and W;

$X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y, and even more preferably, $X_7$, and $X_9$ being selected from the group consisting of A, D, N, C, G, Q, H, L, K, M, F, S, W and Y; and the other residues are as defined above.

More particularly, the peptide molecule can comprise the elements E1-B-E2, in which either:

$X_1$ and $X_2$ are absent;

$X_3$ is I, R or L, preferably I or L;

$X_4$ is T or M, preferably T;

$X_5$ is P;

$X_6$ is E or D, preferably D;

$X_7$ is selected from the group consisting of R, A, I and E, and preferably R, A and E;

$X_8$ is selected from the group consisting of R, Q and E;

$X_9$ is R or A;

$X_{10}$ is R; and $X_{11}$ is R or E;

or $X_1$, $X_7$ and $X_9$ are A;

$X_2$ is S;

$X_3$ is T;

$X_4$, $X_5$, $X_8$ are E or R;

$X_6$ is W;

$X_{10}$ is R; and $X_{11}$ is R or A;

and $X_{12}$ is A or P;

$X_{13}$ is absent or selected from the amino acids G, A and S;

$X_{14}$ is absent or S;

$X_{15}$ is R, V or A;

$X_{16}$ is T or V;

$X_{17}$ is L;

$X_{18}$ is Y, N or D;

$X_{19}$ is F or M; and $X_{20}$ is selected from the group consisting of G, Q and N.

More particularly, the peptide molecule can also comprise the elements E1-B-E2, in which either:

$X_1$ and $X_2$ are absent;

$X_3$ is I, R or L, preferably I or L;

$X_4$ is T or M, preferably T;

$X_5$ is P;

$X_6$ is E or D, preferably D;

$X_7$ is selected from the group consisting of R, A, I and E, and preferably R, A and E;

$X_8$ is selected from the group consisting of R, Q and E;
$X_9$ is R or A;
$X_{10}$ is R; and
$X_{11}$ is R or E;
or
$X_1$, $X_7$ and $X_9$ are A;
$X_2$ is S;
$X_3$ is T;
$X_4$ is E or R;
$X_6$ is W;
$X_8$ is E; and
$X_5$, $X_{10}$ and $X_{11}$ are R;
and
$X_{12}$ is A or P;
$X_{13}$ is absent or selected from the amino acids G, A and S;
$X_{14}$ is absent or S;
$X_{15}$ is R or V;
$X_{16}$ is T or V;
$X_{17}$ is L;
$X_{18}$ is Y, N or D;
$X_{19}$ is selected from the group consisting of F, M, A and Q, preferably it is F or M, and even more preferably it is F; and
$X_{20}$ is selected from the group consisting of G, Q and N.

Otherwise expressed, the present invention therefore relates to a peptide molecule comprising or consisting of the elements E1-B-E2, in which the elements E1-B-E2 have one of the following two formulas:

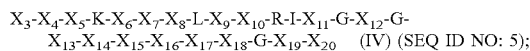    (IV) (SEQ ID NO: 5);

wherein:
$X_3$ is a hydrophobic amino acid or R, preferably selected from the group consisting of A, C, V, P, L, I, M, F, W, R and Y, even more preferably from the group consisting of A, C, V, P, L, I, M, F, W and Y;
$X_4$ is an amino acid selected from the group consisting of T, S, P, D, M and N, preferably from the group consisting of T, S, P, D and N;
$X_6$ is an amino acid selected from the group consisting of Q, E, L, M, A, D and W, preferably from the group consisting of Q, E, L, M, A and W;
$X_7$, $X_8$ and $X_9$, independently of each other, are any amino acid, preferably selected from the natural amino acids (A, R, D, N, C, G, Q, E, H, I, L, K, M, F, P, S, T, V, W and Y), provided that at least two of the residues $X_7$, $X_8$ and $X_9$ are an amino acid favorable to an alpha helix secondary structure, preferably selected from the group consisting of A, R, D, N, C, G, Q, E, H, L, K, M, F, S, W and Y;
$X_5$, $X_{10}$, $X_{11}$, $X_{12}$, and $X_{17}$, independently of each other, are any amino acid, preferably selected from the natural amino acids (A, R, D, N, C, G, Q, E, H, I, L, K, M, F, P, S, T, V, W and Y);
$X_{13}$ is absent or selected from the amino acids G, A and S;
$X_{14}$ is absent or is any amino acid, preferably selected from the natural amino acids (A, R, D, N, C, G, Q, E, H, I, L, K, M, F, P, S, T, V, W and Y);
$X_{15}$ is R or V;
$X_{16}$ is T or V;
$X_{18}$ is any non-positively charged amino acid, preferably selected from the group consisting of A, D, N, C, G, Q, E, H, I, L, M, F, P, S, T, V, W and Y;
$X_{19}$ is a hydrophobic amino acid, preferably selected from the group consisting of A, C, V, P, L, I, M, F, W and Y; and
$X_{20}$, is absent or is any amino acid, preferably selected from the natural amino acids (A, R, D, N, C, G, Q, E, H, I, L, K, M, F, P, S, T, V, W and Y);
or

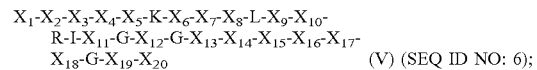    (V) (SEQ ID NO: 6);

wherein:
$X_1$ is absent or is any amino acid, preferably selected from the natural amino acids (A, R, D, N, C, G, Q, E, H, I, L, K, M, F, P, S, T, V, W and Y);
$X_2$ is absent or is any amino acid, preferably selected from the natural amino acids (A, R, D, N, C, G, Q, E, H, I, L, K, M, F, P, S, T, V, W and Y);
$X_3$ is an amino acid selected from the group consisting of T, S, P, D and N;
$X_4$ and $X_5$, independently of each other, are an amino acid favorable to an alpha helix secondary structure, preferably selected from the group consisting of A, R, D, N, C, G, Q, E, H, L, K, M, F, S, W and Y;
$X_6$ is an amino acid selected from the group consisting of Q, E, L, M, A, D and W, preferably from the group consisting of Q, E, L, M, A and W;
$X_7$, $X_8$ and $X_9$, independently of each other, are any amino acid, preferably selected from the natural amino acids (A, R, D, N, C, G, Q, E, H, I, L, K, M, F, P, S, T, V, W and Y), provided that at least two of the residues $X_7$, $X_8$ and $X_9$ are an amino acid favorable to an alpha helix secondary structure, preferably selected from the group consisting of A, R, D, N, C, G, Q, E, H, L, K, M, F, S, W and Y;
$X_{13}$ is absent or selected from the amino acids G, A and S;
$X_{14}$ is absent or is any amino acid, preferably selected from the natural amino acids (A, R, D, N, C, G, Q, E, H, I, L, K, M, F, P, S, T, V, W and Y);
$X_{15}$ is any amino acid, preferably selected from the natural amino acids (A, R, D, N, C, G, Q, E, H, I, L, K, M, F, P, S, T, V, W and Y), preferably from among A, T, V, I and R, even more preferably it is R or V;
$X_{16}$ is T or V;
$X_{10}$, $X_{11}$, $X_{12}$, and $X_{17}$, independently of each other, are any amino acid, preferably selected from the natural amino acids (A, R, D, N, C, G, Q, E, H, I, L, K, M, F, P, S, T, V, W and Y);
$X_{18}$ is any non-positively charged amino acid, preferably selected from the group consisting of A, D, N, C, G, Q, E, H, I, L, M, F, P, S, T, V, W and Y;
$X_{19}$ is a hydrophobic amino acid, preferably selected from the group consisting of A, C, V, P, L, I, M, F, W and Y; and
$X_{20}$, is absent or is any amino acid, preferably selected from the natural amino acids (A, R, D, N, C, G, Q, E, H, I, L, K, M, F, P, S, T, V, W and Y).

In a preferred embodiment, the present invention relates to a peptide molecule comprising or consisting of the elements E1-B-E2 as defined above, in which
either E1 is a peptide of formula (I) (SEQ ID NO: 7) with
$X_1$ and $X_2$ are absent;
$X_3$ is a hydrophobic amino acid selected from the group consisting of A, C, V, P, L, I, M, F, W and Y;
$X_4$ is an amino acid selected from the group consisting of T, S, P, D and N;
$X_5$ is any amino acid, preferably selected from the natural amino acids (A, R, D, N, C, G, Q, E, H, I, L, K, M, F, P, S, T, V, W and Y);
$X_6$ is an amino acid selected from the group consisting of Q, E, L, M, A, and W;

$X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y; and $X_{10}$ and $X_{11}$, independently of each other, are any amino acid, preferably selected from the natural amino acids (A, R, D, N, C, G, Q, E, H, I, L, K, M, F, P, S, T, V, W and Y);

or E1 is a peptide of formula (I) (SEQ ID NO: 8) with $X_1$, $X_2$, $X_{10}$ and $X_{11}$, independently of each other, are any amino acid, preferably selected from the natural amino acids (A, R, D, N, C, G, Q, E, H, I, L, K, M, F, P, S, T, V, W and Y);

$X_4$, $X_5$, $X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y;

$X_3$ is an amino acid selected from the group consisting of T, S, P, D and N; and $X_6$ is an amino acid selected from the group consisting of Q, E, L, M, A, and W.

In this embodiment, the present invention therefore relates to a peptide molecule comprising or consisting of the elements E1-B-E2, in which the elements E1-B-E2 have one of the following two formulas:

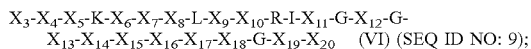
$X_3$-$X_4$-$X_5$-K-$X_6$-$X_7$-$X_8$-L-$X_9$-$X_{10}$-R-I-$X_{11}$-G-$X_{12}$-G-$X_{13}$-$X_{14}$-$X_{15}$-$X_{16}$-$X_{17}$-$X_{18}$-G-$X_{19}$-$X_{20}$   (VI) (SEQ ID NO: 9);

wherein:

$X_3$ is a hydrophobic amino acid selected from the group consisting of A, C, V, P, L, I, M, F, W and Y;

$X_4$ is an amino acid selected from the group consisting of T, S, P, D and N;

$X_6$ is an amino acid selected from the group consisting of Q, E, L, M, A, and W;

$X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y;

$X_{13}$ is absent or selected from the amino acids G, A and S;

$X_{14}$ is absent or is any amino acid, preferably selected from the natural amino acids (A, R, D, N, C, G, Q, E, H, I, L, K, M, F, P, S, T, V, W and Y);

$X_{15}$ is selected from the group consisting of A, T, V, I and R, preferably it is R or V;

$X_{16}$ is T or V;

$X_5$, $X_{10}$, $X_{11}$, $X_{12}$, and $X_{17}$, independently of each other, are any amino acid, preferably selected from the natural amino acids (A, R, D, N, C, G, Q, E, H, I, L, K, M, F, P, S, T, V, W and Y);

$X_{18}$ is any non-positively charged amino acid, preferably selected from the group consisting of A, D, N, C, G, Q, E, H, I, L, M, F, P, S, T, V, W and Y;

$X_{19}$ is a hydrophobic amino acid, preferably selected from the group consisting of A, C, V, P, L, I, M, F, W and Y; and $X_{20}$, is absent or is any amino acid, preferably selected from the natural amino acids (A, R, D, N, C, G, Q, E, H, I, L, K, M, F, P, S, T, V, W and Y) or

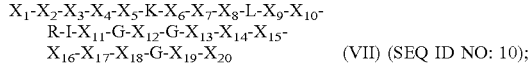
$X_1$-$X_2$-$X_3$-$X_4$-$X_5$-K-$X_6$-$X_7$-$X_8$-L-$X_9$-$X_{10}$-R-I-$X_{11}$-G-$X_{12}$-G-$X_{13}$-$X_{14}$-$X_{15}$-$X_{16}$-$X_{17}$-$X_{18}$-G-$X_{19}$-$X_{20}$   (VII) (SEQ ID NO: 10);

wherein:

$X_4$, $X_5$, $X_7$, $X_8$, and $X_9$, independently of each other, are an amino acid favorable to an alpha helix secondary structure, preferably selected from the group consisting of A, R, D, N, C, G, Q, E, H, L, K, M, F, S, W and Y;

$X_3$ is an amino acid selected from the group consisting of T, S, P, D and N;

$X_6$ is an amino acid selected from the group consisting of Q, E, L, M, A, and W;

$X_{13}$ is absent or selected from the amino acids G, A and S;

$X_{14}$ is absent or is any amino acid, preferably selected from the natural amino acids (A, R, D, N, C, G, Q, E, H, I, L, K, M, F, P, S, T, V, W and Y);

$X_{15}$ is selected from the group consisting of A, T, V, I and R, preferably it is R or V;

$X_{16}$ is T or V;

$X_1$, $X_2$, $X_{10}$, $X_{11}$, $X_{12}$, and $X_{17}$, independently of each other, are any amino acid, preferably selected from the natural amino acids (A, R, D, N, C, G, Q, E, H, I, L, K, M, F, P, S, T, V, W and Y);

$X_{18}$ is any non-positively charged amino acid, preferably selected from the group consisting of A, D, N, C, G, Q, E, H, I, L, M, F, P, S, T, V, W and Y;

$X_{19}$ is a hydrophobic amino acid, preferably selected from the group consisting of A, C, V, P, L, I, M, F, W and Y; and $X_{20}$, is absent or is any amino acid, preferably selected from the natural amino acids (A, R, D, N, C, G, Q, E, H, I, L, K, M, F, P, S, T, V, W and Y).

In a still more preferred embodiment, the present invention relates to a peptide molecule comprising or consisting of the elements E1-B-E2 as defined above, wherein the elements E1-B-E2 have one of the following two formulas:

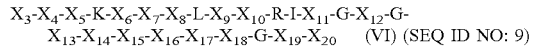
$X_3$-$X_4$-$X_5$-K-$X_6$-$X_7$-$X_8$-L-$X_9$-$X_{10}$-R-I-$X_{11}$-G-$X_{12}$-G-$X_{13}$-$X_{14}$-$X_{15}$-$X_{16}$-$X_{17}$-$X_{18}$-G-$X_{19}$-$X_{20}$   (VI) (SEQ ID NO: 9)

as defined above and in particular having one or more of the following characteristics:

$X_3$ is I, R or L, preferably I or L;
$X_4$ is T or M, preferably T;
$X_5$ is P;
$X_6$ is E or D, preferably D;
$X_7$ is selected from the group consisting of R, A, I and E, preferably R, A and E;
$X_8$ is selected from the group consisting of R, Q and E;
$X_9$ is R or A;
$X_{10}$ is R;
$X_{11}$ is R or E;
$X_{12}$ is A or P;
$X_{13}$ is absent or selected from the amino acids G, A and S;
$X_{14}$ is absent or S;
$X_{15}$ is R or V;
$X_{16}$ is T or V;
$X_{17}$ is L;
$X_{18}$ is Y, N or D;
$X_{19}$ is selected from the group consisting of F, M, A and Q, preferably F or M, even more preferably F; and
$X_{20}$ is selected from the group consisting of G, Q and N; or

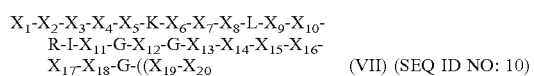
$X_1$-$X_2$-$X_3$-$X_4$-$X_5$-K-$X_6$-$X_7$-$X_8$-L-$X_9$-$X_{10}$-R-I-$X_{11}$-G-$X_{12}$-G-$X_{13}$-$X_{14}$-$X_{15}$-$X_{16}$-$X_{17}$-$X_{18}$-G-(($X_{19}$-$X_{20}$)   (VII) (SEQ ID NO: 10)

as defined above and in particular having one or more of the following characteristics:

$X_1$, $X_7$ and $X_9$ are A;
$X_2$ is S;
$X_3$ is T;
$X_4$ is E or R;
$X_6$ is W;
$X_8$ is E;
$X_5$, $X_{10}$ and $X_{11}$ are R;

$X_{12}$ is A or P;
$X_{13}$ is absent or selected from the amino acids G, A and S;
$X_{14}$ is absent or S;
$X_{15}$ is R or V;
$X_{16}$ is T or V;
$X_{17}$ is L;
$X_{18}$ is Y, N or D;
$X_{19}$ is selected from the group consisting of F, M, A and Q, preferably F or M, even more preferably F; and
$X_{20}$ is selected from the group consisting of G, Q and N.

In a particularly preferred embodiment, the present invention relates to a peptide molecule comprising or consisting of the elements E1-B-E2 as defined above, wherein the elements E1-B-E2 have one of the following formulas:

$X_3$-$X_4$-P-K-$X_6$-$X_7$-$X_8$-L-$X_9$-R-R-I-$X_{11}$-G-$X_{12}$-G-$X_{13}$-$X_{14}$-$X_{15}$-$X_{16}$-L-$X_{18}$-G-$X_{19}$-$X_{20}$   (VIII) (SEQ ID NO: 11);

wherein:
$X_3$ is I, R or L, preferably I or L;
$X_4$ is T or M, preferably T;
$X_6$ is E or D, preferably D;
$X_7$ is selected from the group consisting of R, A, I and E, preferably from R, A and E;
$X_8$ is selected from the group consisting of R, Q and E;
$X_9$ is R or A;
$X_{11}$ is R or E;
$X_{12}$ is A or P;
$X_{13}$ is absent or selected from the amino acids G, A and S;
$X_{14}$ is absent or S;
$X_{15}$ is R or V;
$X_{16}$ is T or V;
$X_{18}$ is Y, N or D;
$X_{19}$ is selected from the group consisting of F, M, A et Q, preferably F or M, even more preferably F; and
$X_{20}$ is selected from the group consisting of G, Q and N,
or A-S-T-$X_4$-R—K-W-A-E-L-A-R—R-I-R-G-$X_{12}$-G-$X_{13}$-$X_{14}$-$X_{15}$-$X_{16}$-L-$X_{18}$-G-$X_{19}$-$X_{20}$   (IX) (SEQ ID NO: 12);

wherein:
$X_4$ is E or R;
$X_{12}$ is A or P;
$X_{13}$ is absent or selected from the amino acids G, A and S;
$X_{14}$ is absent or S;
$X_{15}$ is R or V;
$X_{16}$ is T or V;
$X_{18}$ is Y, N or D;
$X_{19}$ is selected from the group consisting of F, M, A and Q, preferably F or M, even more preferably F; and
$X_{20}$ is selected from the group consisting of G, Q and N,
or A-S-T-$X_4$-$X_5$-K-W-A-E-L-A-$X_8$-R-I-$X_{11}$-G-$X_{12}$-G-$X_{13}$-$X_{14}$-$X_{15}$-$X_{16}$-L-$X_{18}$-G-$X_{19}$-$X_{20}$   (XI) (SEQ ID NO: 82);

wherein:
$X_4$, $X_5$, $X_8$ are E or R;
$X_{11}$ is R or A;
$X_{12}$ is A or P;
$X_{13}$ is absent or selected from the amino acids G, A and S;
$X_{14}$ is absent or S;
$X_{15}$ is R, V or A;
$X_{16}$ is T or V;
$X_{18}$ is Y, N or D;
$X_{19}$ is F or M, preferably F; and
$X_{20}$ is selected from the group consisting of G, Q and N.

In a particular embodiment, the present invention relates to a peptide molecule comprising or consisting of the elements E1-B-E2 as defined above, in which the elements E1-B-E2 have one of the following sequences:

```
                              (SEQ ID NO: 13)
IMPKDIQLARRIRGAGGRTLYGFG (SEQ ID NO: 14)
IMPKDIQLARRIRGAGASRTLYGFG (SEQ ID NO: 15)
ITPKEAQLARRIRGAGGRTLNGFG (SEQ ID NO: 16)
ITPKEAQLARRIRGAGASRTLNGFG (SEQ ID NO: 17)
LTPKEAELARRIRGAGGRTLNGFG (SEQ ID NO: 18)
LTPKEAELARRIRGAGASRTLNGFG (SEQ ID NO: 19)
ITPKEAQLARRIEGAGASVTLNGFG (SEQ ID NO: 20)
LTPKEAELARRIEGAGASVTLNGFG (SEQ ID NO: 21)
ITPKEEQLRRRIEGAGASVTLNGFG (SEQ ID NO: 22)
ITPKEAQLARRIRGAGGVTLNGFG (SEQ ID NO: 23)
LTPKEAELARRIRGAGGVTLNGFG (SEQ ID NO: 24)
LTPKEAELARRIRGAGRTLNGFG (SEQ ID NO: 25)
LTPKEAELARRIRGAGGRTLNGFG (SEQ ID NO: 26)
LTPKEAELARRIRGAGASRTLNGFG (SEQ ID NO: 27)
RTPKERRLARRIRGAGGRTLNGFG (SEQ ID NO: 28)
RTPKEARLARRIRGAGGRTLNGFG (SEQ ID NO: 29)
LTPKEAELARRIRGAGGVTYDGFG (SEQ ID NO: 30)
LTPKEAELARRIRGAGGVTLNGAN (SEQ ID NO: 31)
STERKWAELARRIRGAGGVTLNGFG (SEQ ID NO: 32)
ASTERKWAELARRIRGAGGVTLNGFG (SEQ ID NO: 33)
ASTRRKWAELARRIRGAGGVTLNGFG, (SEQ ID NO: 75)
ASTEEKWARLARRIRGAGGVTLNGFG (SEQ ID NO: 76)
ASTERKWAELARRIRGAGGVTLDGFG (SEQ ID NO: 77)
ASTERKWAELARRIRGAGGRTLNGFG (SEQ ID NO: 78)
ASTERKWAELARRIRGAGGATLNGFG
```

ASTERKWAELARRIAGAGGVTLNGFG (SEQ ID NO: 79)

ASTEEKWARLARRIAGAGGVTLDGFG (SEQ ID NO: 80)

as well as a sequence having 90 or 95% identity therewith.

In the spirit of the invention, "percent identity" is intended to mean a percentage of amino acid residues identical between the two compared sequences, this percentage being obtained after implementing the best alignment (optimum alignment) between the two sequences. One skilled in the art knows different techniques allowing them to obtain such a percent identity and involving homology algorithms or computer programs such as the Needleman-Wunsch global alignment algorithm by taking into account any "gaps", the NCBI BLAST program or the alignment tool "EMBOSS Pairwise Alignment Algorithms" available in particular on the EMBL-EBI website. In particular, the percentage of identity to the reference sequence is determined by dividing (i) the total number of identical aligned residues between the two sequences by (ii) the total number of residues in the reference sequence, then multiplying the resulting quotient by 100.

Preferably, the peptide molecule according to the present invention further comprises an element facilitating the penetration of the molecule into the cell. In particular, this element is a peptide facilitating the cell penetration of the molecule (CPP: cell-penetrating peptide element). These peptides are well known to one skilled in the art (for example, Vivés et al., Biochimica et Biophysica Acta, 2008, 1786, 126-138). For example and not by way of limitation, the peptide facilitating cell penetration can be chosen from the group consisting of a Tat peptide, in particular RKKRRQRRR (SEQ ID NO: 34), an antennapedia or penetratin peptide, in particular RQIKIWFQNRRMKWKK (SEQ ID NO: 35), and a peptide rich in arginine and lysine, preferably rich in arginine, in particular a peptide comprising at least 9 arginine residues such as a poly-arginine RRRRRRRRR (SEQ ID NO: 36) or RRPRRPRRPRRPRRP (SEQ ID NO: 37).

This peptide facilitating cell penetration of the molecule can be present on the N-terminal or C-terminal side of the elements E1-B-E2, preferably on the N-terminal side thereof. It can either be directly linked to the elements E1-B-E2, or can be linked thereto through a peptide.

Optionally, the peptide molecule can also comprise other peptide sequences, on the N-terminal or C-terminal side of the elements E1-B-E2 and/or between these elements and the peptide facilitating cell penetration and/or at the extremity of the peptide facilitating cell penetration.

In one very particular embodiment, the peptide molecule comprises or consists of a sequence selected from the group consisting of:

GAMGTIMPKDIQLARRIRGAGGRTLYGFG (SEQ ID NO: 38)

GAMGTIMPKDIQLARRIRGAGASRTLYGFG (SEQ ID NO: 39)

GAMGTITPKEAQLARRIRGAGGRTLNGFG (SEQ ID NO: 40)

GAMGTITPKEAQLARRIRGAGASRTLNGFG (SEQ ID NO: 41)

GAMGTLTPKEAELARRIRGAGGRTLNGFG (SEQ ID NO: 42)

GAMGTLTPKEAELARRIRGAGASRTLNGFG (SEQ ID NO: 43)

GAMGTITPKEAQLARRIEGAGASVTLNGFG (SEQ ID NO: 44)

GAMGTLTPKEAELARRIEGAGASVTLNGFG (SEQ ID NO: 45)

GAMGTITPKEEQLRRRIEGAGASVTLNGFG (SEQ ID NO: 46)

GAMGTITPKEAQLARRIRGAGGVTLNGFG (SEQ ID NO: 47)

GAMGTLTPKEAELARRIRGAGGVTLNGFG (SEQ ID NO: 48)

GAMGTLTPKEAELARRIRGAGRTLNGFG (SEQ ID NO: 49)

GAMGTLTPKEAELARRIRGAGASRTLNGFG (SEQ ID NO: 51)

GAMGLTAAEHAKRSTLTPKEAQLARRIRGAGGVTLNGFG (SEQ ID NO: 52)

LTAAEHAKRSTLTPKEAELARRIRGAGGVTLNGFG (SEQ ID NO: 53)

LTAAEHAKRSTLTPKEAQLARRIEGAGASVTLNGFG (SEQ ID NO: 54)

LTAAEHAKRSTLTPKEAELARRIEGAGASVTLNGFG (SEQ ID NO: 55)

GAMGTRTPKERRLARRIRGAGGRTLNGFG (SEQ ID NO: 56)

GAMGTRTPKEARLARRIRGAGGRTLNGFG (SEQ ID NO: 57)

GRKKRRQRRRGAMGTITPKEAQLARRIRGAGGVTLNGFG (SEQ ID NO: 58)

RRPRRPRRPRRPRRPGAMGTITPKEAQLARRIRGAGGVTLNGFG (SEQ ID NO: 59)

GAMGTLTPKEAELARRIRGAGGVTYDGFG (SEQ ID NO: 61)

GAMGTLTPKEAELARRIRGAGGVTLNGFGASTG (SEQ ID NO: 62)

GAMGTLTPKEAELARRIRGAGGVTLNGANFVSTG (SEQ ID NO: 63)

GAMGRVPPAVRKLGNSTERKWAELARRIRGAGGVTLNGFG (SEQ ID NO: 64)

GAMGRVPPAVRKLGNASTERKWAELARRIRGAGGVTLNGFG (SEQ ID NO: 65)

ASTERKWAELARRIRGAGGVTLNGFG (SEQ ID NO: 32)

ASTRRKWAELARRIRGAGGVTLNGFG (SEQ ID NO: 33)

ASTEEKWARLARRIRGAGGVTLNGFG (SEQ ID NO: 75)

ASTERKWAELARRIRGAGGVTLDGFG (SEQ ID NO: 76)

ASTERKWAELARRIRGAGGRTLNGFG (SEQ ID NO: 77)

ASTERKWAELARRIRGAGGATLNGFG (SEQ ID NO: 78)

ASTERKWAELARRIAGAGGVTLNGFG (SEQ ID NO: 79)

ASTEEKWARLARRIAGAGGVTLDGFG (SEQ ID NO: 80)

RRPRRPRRPRRPRRPASTERKWAELARRIRGAGGVTLNGFGGCA (SEQ ID NO: 66)

RRPRRPRRPRRPRRPASTERKWAELARRIRGAGGVTLNGFG (SEQ ID NO: 67)

RRPRRPRRPRRPRRPGAMGTITPKEAQLARRIRGAGGVTLNGFGCA (SEQ ID NO: 50)
and

RRPRRPRRPRRPRRPASTEEKWARLARRIAGAGGVTLDGFG (SEQ ID NO: 81)

as well as a sequence having 90 or 95% identity therewith.

In a particularly preferred embodiment, the peptide molecule comprises or consists of a sequence selected from the group consisting of:

RRPRRPRRPRRPRRPGAMGTITPKEAQLARRIRGAGGVTLNGFGCA (SEQ ID NO: 50)

RRPRRPRRPRRPRRPGAMGTITPKEAQLARRIRGAGGVTLNGFG (SEQ ID NO: 59)

RRPRRPRRPRRPRRPASTERKWAELARRIRGAGGVTLNGFGGCA (SEQ ID NO: 66)
and

RRPRRPRRPRRPRRPASTERKWAELARRIRGAGGVTLNGFG (SEQ ID NO: 67)
and

RRPRRPRRPRRPRRPASTEEKWARLARRIAGAGGVTLDGFG (SEQ ID NO: 81).

The peptide molecule according to the present invention can comprise non-natural amino acids. "Non-natural amino acid" is understood to mean an analogue or derivative of a natural amino acid. For example, a non-natural amino acid can have a longer, shorter, or variant side chain having suitable functional groups.

Of course, the L and D isomers of amino acids are considered. In fact, the D isomers are not sensitive to proteases and the present invention also comprises molecules comprising only or mainly D amino acids. In a particular embodiment, the L amino acids are preferred.

The peptide sequences defined herein are represented by a one-letter symbol as shown below:

| A | Ala | (alanine) |
| R | Arg | (arginine) |
| N | Asn | (asparagine) |
| D | Asp | (aspartic acid) |
| C | Cys | (cysteine) |
| Q | Gln | (glutamine) |
| E | Glu | (glutamic acid) |
| G | Gly | (glycine) |
| H | His | (histidine) |
| I | Ile | (isoleucine) |
| L | Leu | (leucine) |
| K | Lys | (lysine) |
| M | Met | (methionine) |
| F | Phe | (phenylalanine) |
| P | Pro | (proline) |
| S | Ser | (serine) |
| T | Thr | (threonine) |
| W | Trp | (tryptophan) |
| Y | Tyr | (tyrosine) |
| V | Val | (valine) |

In addition, some or all peptide bonds of the peptide molecule according to the present invention can be modified to make them resistant to proteolysis. For example, at least one peptide linkage (—CO—NH—) can be replaced by a divalent linkage selected from (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N═N—), and (—CH═CH—). Optionally, all the peptide linkages can be replaced.

The peptide molecule can comprise either a C-terminal carboxylic (—COO$^-$) or amide (—CONH$_2$). The peptide can also be optionally modified at its N-terminal end, for example with an acetyl group.

In addition, the peptide molecule according to the present invention can be modified to make it more stable, and in particular more resistant to proteases. Thus, the molecule can carry PEG (polyethylene glycol) groups. PEGylation methods are well known to one skilled in the art (Olson et al., 2009, Integrative Biology, 1(5-6): p. 382-393).

"Amino acid favorable to an alpha helix structure" is understood to mean in particular an amino acid that is suitable or conducive to the adoption of an alpha helical secondary structure. In particular, this excludes the amino acids unfavorable to this secondary structure such T, V, P and I. Thus, this residue can be selected from the list consisting of A, R, D, N, C, G, Q, E, H, L, K, M, F, S, W and Y, preferably from A, R, D, N, C, Q, E, H, L, K, M, F, S, and W, still more preferably a combination of amino acids can be selected using software to predict the stability of helical structures well known to one skilled in the art, such as AGADIR.

Preferably, the peptide molecule has a maximum size of 200, 150 or 100 amino acids.

The present invention also relates to a nucleic acid coding for a peptide molecule according to the invention and an expression cassette or an expression vector comprising this nucleic acid and capable of expressing and producing said molecule in appropriate conditions. Thus, the peptide molecule can be produced by genetic engineering. Alternatively, the molecule can also be produced by a method of peptide synthesis well known to one skilled in the art.

The present invention also relates to a peptide molecule according to the present invention as a medicament. Preferably, the present invention relates to a peptide molecule according to the present invention as an anticancer agent or agent sensitizing cancer cells to anticancer agents.

The present invention relates to a pharmaceutical composition comprising a peptide molecule according to the present invention and a pharmaceutically acceptable carrier. Optionally, the composition can also comprise another therapeutic agent, particularly an anticancer agent. Preferably, the composition is intended for treating cancer.

The present invention relates to a peptide molecule according to the present invention for use in the treatment or prevention of cancer, optionally in combination with another therapeutic agent, in particular an anticancer agent, and/or with radiotherapy. Thus, the present invention also relates to a product or kit comprising a peptide molecule according to the present invention and an anticancer agent as a combined preparation for simultaneous, separate or sequential use, in particular for use in the treatment of cancer.

Furthermore, the present invention also relates to the use of a peptide molecule according to the present invention for preparing a medicament for the treatment or prevention of cancer, optionally in combination with another therapeutic agent, in particular an anticancer agent and/or with radiotherapy.

Finally, the present invention relates to a method for treating cancer in a patient, comprising administering to the patient a therapeutically effective amount of a peptide molecule according to the present invention. Optionally, the method can further comprise administering another anticancer agent and/or treatment with radiotherapy.

In the context of the present invention, the term "treatment" or "treating" includes preventive, curative, and palliative treatment and management of patients (reducing pain, improving survival, slowing disease progression, reducing tumor growth, decreasing tumor size, preventing or reducing metastases and relapses, etc.).

Cancers include solid tumor cancers or hematopoietic cancers. Cancers can be selected, non-exhaustively, from breast cancers, osteocarcinomas, cancers of the skin, ovaries, lung, uterus, cervix, vagina, prostate, testicles, thyroid, lymphatic system, blood, liver, pancreas, kidney, bladder, brain or colon, and gastric cancers.

The present application relates to the combination of the molecule according to the present invention with another anticancer agent that can be selected from chemotherapy, radiotherapy, hormone therapy, immunotherapy, and gene therapy.

The treatments and medicaments of the invention are particularly intended for humans.

The molecules or compositions according to the invention can be administered in different ways and in different forms. Thus, they can be administered systemically, orally, by inhalation or by injection, such as intravenously, intramuscularly, subcutaneously, transdermally, intra-arterially, etc., the intravenous, intramuscular, subcutaneous, oral and inhalation routes being preferred. For injections, the molecules are usually packaged in the form of liquid suspensions, which can be injected through syringes or infusions, for example. In this regard, the molecules are usually dissolved in saline, physiological, isotonic, or buffered solutions, etc., compatible with pharmaceutical use and known to one skilled in the art. Thus, the compositions can contain one or more agents, carriers or vehicles chosen from dispersants, solubilizers, stabilizers, preservatives, etc. Agents or vehicles that can be used in liquid and/or injectable formulations include in particular methylcellulose, hydroxymethylcellulose, carboxymethylcellulose, polysorbate 80, mannitol, gelatin, lactose, vegetable oils, acacia, etc.

The molecules can also be administered in the form of gels, oils, tablets, suppositories, powders, capsules, pills, aerosols, etc., possibly by means of dosage forms or devices providing extended and/or delayed release. For this type of formulation, an agent such as cellulose, a carbonate or a starch is advantageously used.

By "effective amount" is meant the amount which is necessary to prevent, eliminate or reduce the adverse effects of cancer. It is understood that the flow rate and/or the injected dose can be adapted by one skilled in the art according to the patient, the pathology concerned, the method of administration, etc. Typically, the molecules are administered at doses that can range from 1 µg to 1000 mg/kg of body weight, more generally from 10 µg to 100 mg/kg, typically between 1 mg and 20 mg/kg. In addition, repeated injections can be performed, if necessary. On the other hand, for chronic treatments, delayed or extended release systems may be advantageous.

The examples illustrate the present invention and are not intended to limit it.

DESCRIPTION OF FIGURES

FIG. 4.

EXAMPLES

Results

Design Strategy

Figure 1A:
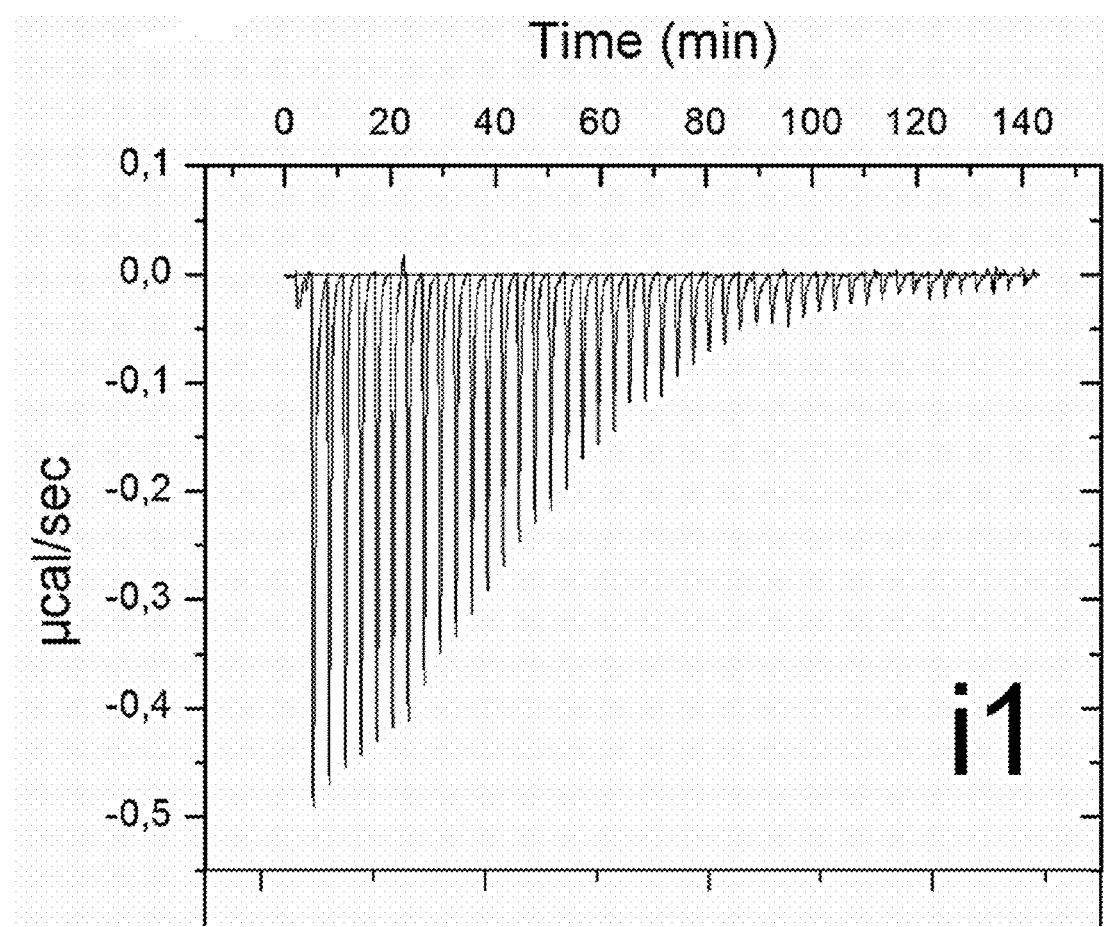
FIG. 1: ITC curves of the interaction Asf1 1-156 (30 µM in A, 10 µM in B and C) with peptide i1 (A), i4 (B) and i5 (C). The peptide concentration used for this experiment is 0.5 mM for i1, and 0.16 mM for i4 and i5.

The strategy adopted by the inventors was to mimic not a partner, but several partners and to optimize by the most rigid link possible for coupling of the binding epitopes of each partner in order to increase the affinity of the chimeric molecule thus generated. This rational design was performed in silico, then validated by several complementary biophysical methods. Finally, the characterization of the biological activity was carried out on human cells in culture.

Design Optimization of the Peptide Inhibitor of the H3H4 Interaction:

The aim of the invention is the design of a peptide inhibitor of the interaction between the Asf1 chaperone and histones H3 and H4. To this end, the inventors coupled the Asf1 binding epitopes of histones H3 and H4 between themselves. To do this, the α3 helix of histone H3 (peptide i1, SEQ ID NO: 70) was connected to the C-terminal β strand of histone H4 by a peptide loop, the length and composition of which have been optimized. Several amino acids of the H3 and H4 epitopes were modified in order to stabilize the bound form of the peptide, making it more soluble and more resistant to proteases so as to improve its lifetime in human cells. The inventors obtained in this manner a series of peptides denoted i4, i4_1, i4_2, i4V, i42V. Finally, certain modifications of the sequence were made to optimize the interaction of the peptide with Asf1 (peptide i5, SEQ ID NO: 32).

Schematic Design of the Peptide
Starting Peptide: Fragment of Histone H3

```
                              SEQ ID NO: 70 (i1)
        GAMGTIMPKDIQLARRIRG
        Kd = 8.7 µM
``` the presence of the GAMG residues resulting from the cloning vector used.

```
Stabilization of the peptide
                                      SEQ ID NO: 71
GAMGTITPKEAQLARRIRG
Kd = 1.4 µM SEQ ID NO: 72
GAMGTLTPKEAELARRIRG
Kd = 2.23 µM Peptides coupling the H3 domain to the H4 domain
via a loop
                                 SEQ ID NO: 38 (i4_1)
GAMGTIMPKDIQLARRIRGAGGRTLYGFG
Kd = 0.56 µM SEQ ID NO: 39
GAMGTIMPKDIQLARRIRGAGASRTLYGFG
Kd = 0.35 µM SEQ ID NO: 40 (i4_2)
GAMGTITPKEAQLARRIRGAGGRTLNGFG
Kd = 0.22 µM SEQ ID NO: 41
GAMGTITPKEAQLARRIRGAGASRTLNGFG
Kd = 0.80 µM SEQ ID NO: 42 (i4)
GAMGTLTPKEAELARRIRGAGGRTLNGFG
Kd = 0.18 µM SEQ ID NO: 43
GAMGTLTPKEAELARRIRGAGASRTLNGFG
Kd = 0.35 µM Peptides more resistant to proteases
                                      SEQ ID NO: 44
GAMGTITPKEAQLARRIEGAGASVTLNGFG
Kd = 0.66 µM SEQ ID NO: 45
GAMGTLTPKEAELARRIEGAGASVTLNGFG
Kd = 2.00 µM SEQ ID NO: 46
GAMGTITPKEEQLRRRIEGAGASVTLNGFG
Kd = 0.42 µM SEQ ID NO: 47 (i42V)
GAMGTITPKEAQLARRIRGAGGVTLNGFG
Kd = 0.35 µM SEQ ID NO: 48 (i4V)
GAMGTLTPKEAELARRIRGAGGVTLNGFG
Kd = 0.06 µM Test on loop lengths
                                      SEQ ID NO: 73
GAMGTLTPKEAELARRIRGARTLNGFG
Kd = 3.89 µM SEQ ID NO: 49
GAMGTLTPKEAELARRIRGAGRTLNGFG
Kd = 0.95 µM SEQ ID NO: 42
GAMGTLTPKEAELARRIRGAGGRTLNGFG
Kd = 0.18 µM SEQ ID NO: 51
GAMGTLTPKEAELARRIRGAGASRTLNGFG
Kd = 0.35 µM SEQ ID NO: 74
GAMGTLTPKEAELARRIRGAGASGRTLNGFG
Kd = 1.89 µM Test on N-terminal elongation
                                      SEQ ID NO: 52
GAMGLTAAEHAKRSTLTPKEAQLARRIRGAGGVTLNGFG
Kd = 0.03 µM SEQ ID NO: 53
LTAAEHAKRSTLTPKEAELARRIRGAGGVTLNGFG
Kd = 0.06 µM SEQ ID NO: 54
LTAAEHAKRSTLTPKEAQLARRIEGAGASVTLNGFG
Kd = 0.12 µM SEQ ID NO: 55
LTAAEHAKRSTLTPKEAELARRIEGAGASVTLNGFG
Kd = 0.88 µM Test to transform the peptide to a cell-
penetrating peptide (CPP)
                                      SEQ ID NO: 56
GAMGTRTPKERRLARRIRGAGGRTLNGFG
Kd = 0.03 µM SEQ ID NO: 57
GAMGTRTPKEARLARRIRGAGGRTLNGFG
Kd = 0.26 µM Test for the addition of cell-penetrating
peptides (CPP)
                                 SEQ ID NO: 58 (TAT-i42V)
GRKKRRQRRRGAMGTITPKEAQLARRIRGAGGVTLNGFG
Kd = 0.62 µM SEQ ID NO: 59 (RRP5-i42V)
RRPRRPRRPRRPRRPGAMGTITPKEAQLARRIRGAGGVTLNGFG
Kd = 0.59 µM SEQ ID NO: 60 (RRP5-i1)
RPRRPRRPRRPRRPGAMGTIMPKDIQLARRIRGGCA
Kd = 0.46 µM SEQ ID NO: 50 (RRP5-i42V-CA)
RRPRRPRRPRRPRRPGAMGTITPKEAQLARRIRGAGGVTLNGFGCA
Kd = 0.42 µM Test on C-terminal elongation
                                      SEQ ID NO: 61
GAMGTLTPKEAELARRIRGAGGVTYDGFG
Kd = 0.10 µM SEQ ID NO: 62
GAMGTLTPKEAELARRIRGAGGVTLNGFGASTG
Kd = 0.32 µM
```

-continued

SEQ ID NO: 63
GAMGTLTPKEAELARRIRGAGGVTLNGANFVSTG
Kd = 1.68 µM

Optimization of binding to Asf1

SEQ ID NO: 64
GAMGRVPPAVRKLGNSTERKWAELARRIRGAGGVTLNGFG
Kd = 0.08 µM

SEQ ID NO: 65
GAMGRVPPAVRKLGNASTERKWAELARRIRGAGGVTLNGFG
Kd = 0.06 µM

SEQ ID NO: 32 (i5)
ASTERKWAELARRIRGAGGVTLNGFG
Kd = 0.04 µM

SEQ ID NO: 33
ASTRRKWAELARRIRGAGGVTLNGFG
Kd = 1.33 µM

SEQ ID NO: 66 (RRP5-i5)
RRPRRPRRPRRPRRPASTERKWAELARRIRGAGGVTLNGFGGCA
Kd = 0.67 µM

SEQ ID NO: 75 (i5_s3)
ASTEEKWARLARRIRGAGGVTLNGFG
Kd = 0.02 µM

SEQ ID NO: 76 (i5_D)
ASTERKWAELARRIRGAGGVTLDGFG
Kd = 0.009 µM

SEQ ID NO: 77 (i5_loopR)
ASTERKWAELARRIRGAGGRTLNGFG
Kd = 0.029 µM

SEQ ID NO: 78 (i5_loopA)
ASTERKWAELARRIRGAGGATLNGFG
Kd = 0.063 µM

SEQ ID NO: 79 (i5_Aloop)
ASTERKWAELARRIAGAGGVTLNGFG
Kd = 0.027 µM

SEQ ID NO: 80 (i6)
ASTEEKWARLARRIAGAGGVTLDGFG
Kd = 0.003 µM

SEQ ID NO: 81 (RRP5-i6)
RRPRRPRRPRRPRRPASTEEKWARLARRIAGAGGVTLDGFG

Figure 1B:
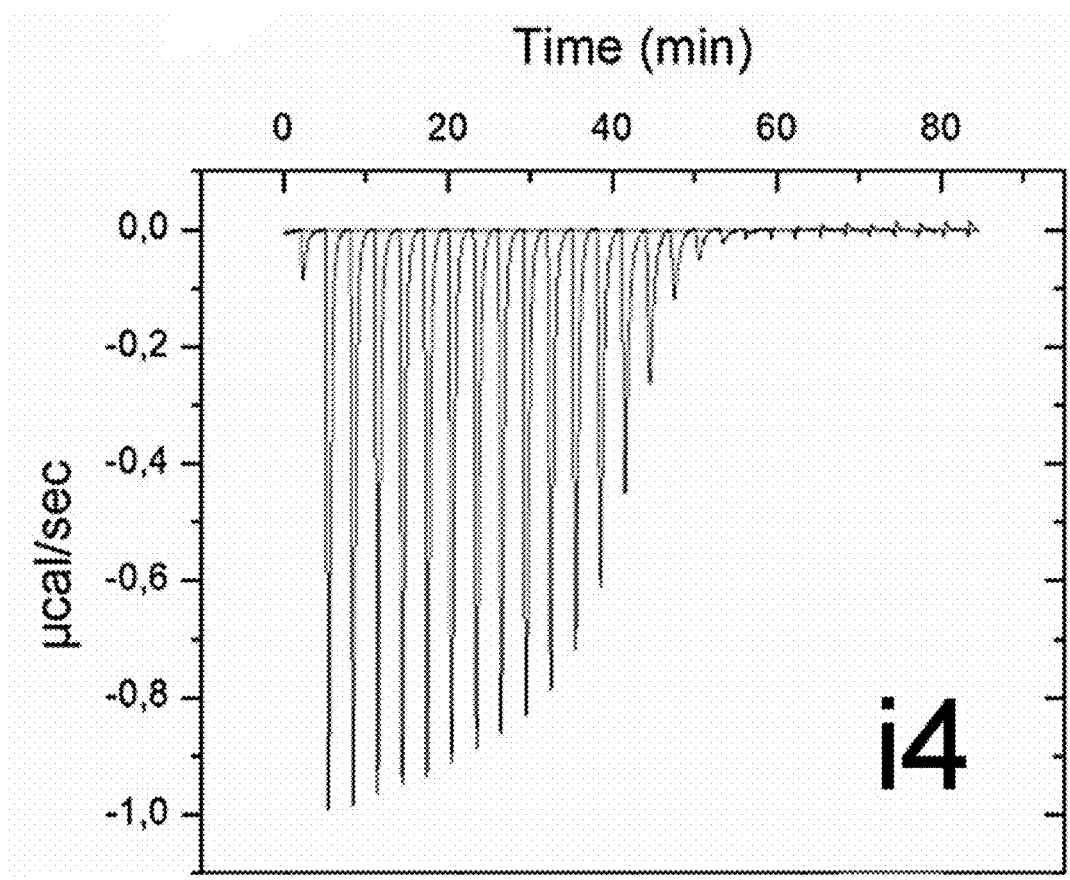
Figure 1C:
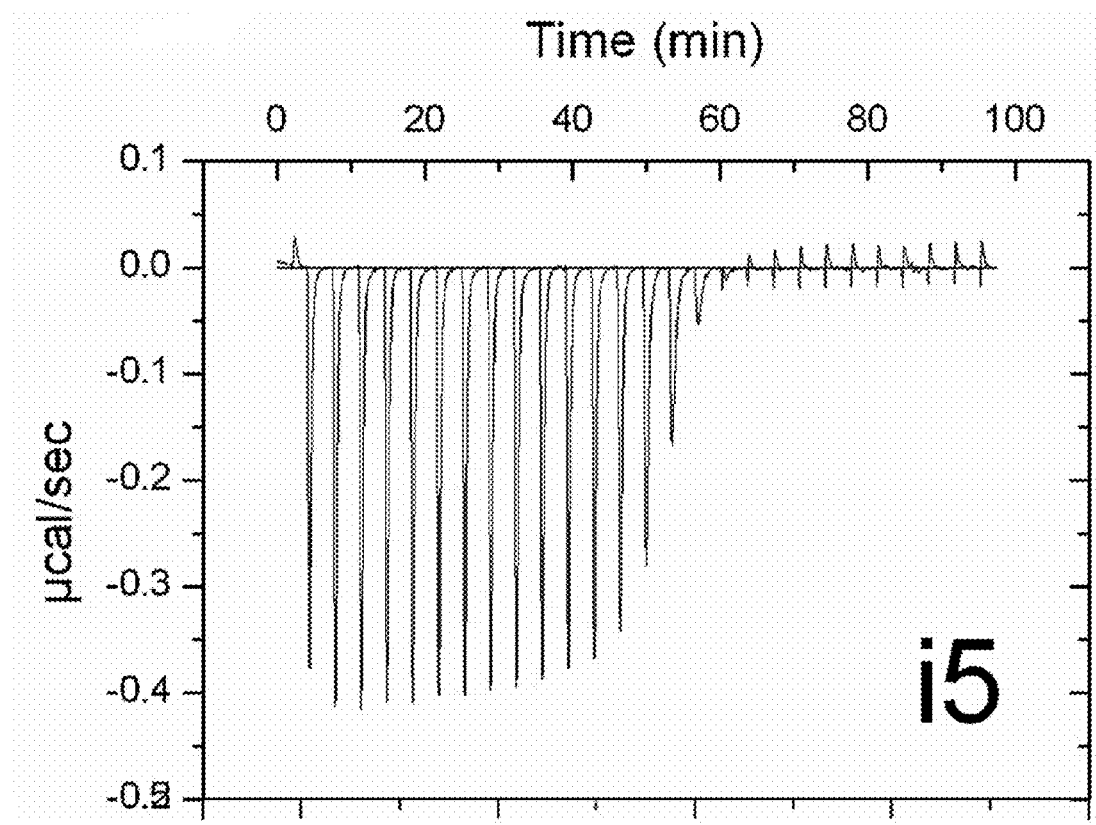
Figure 2A:
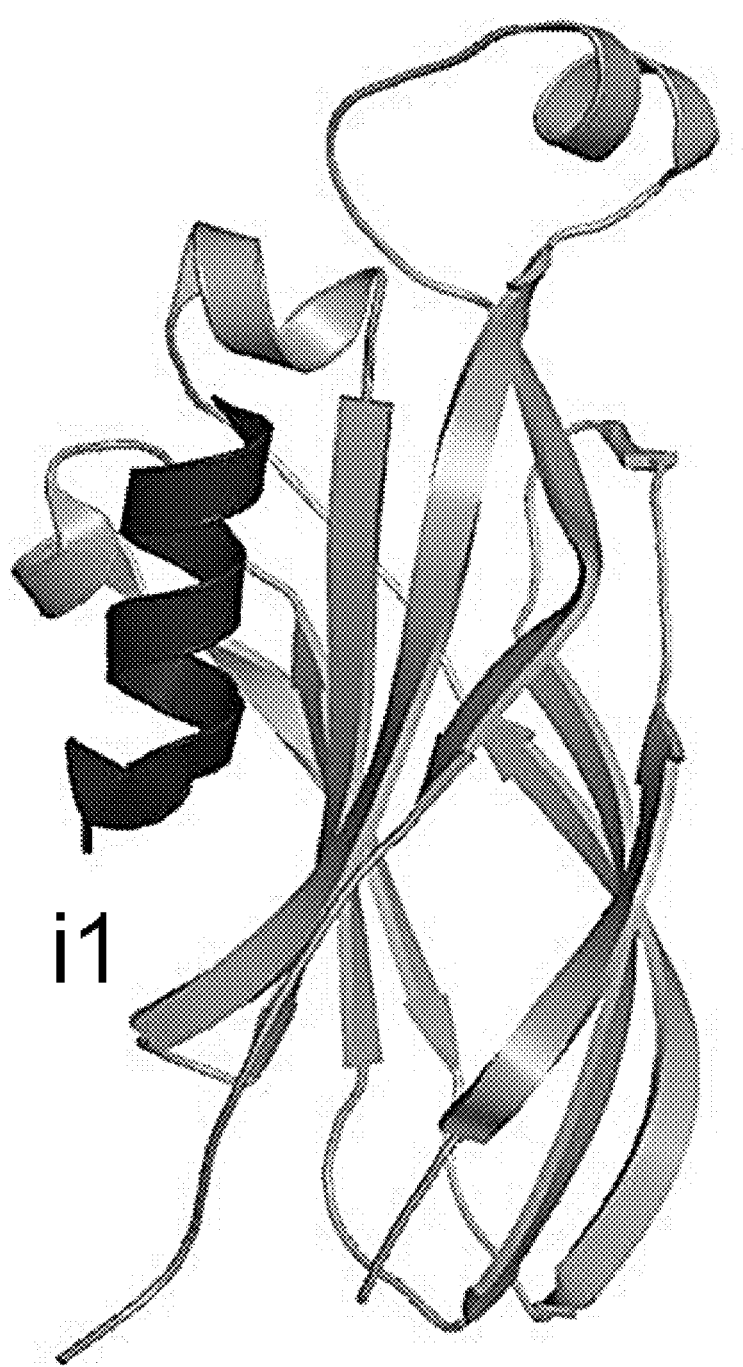
FIG. 2: NMR (A) and crystallographic structure (B and C) of Asf1 in interaction with peptide i1 (A), i4 (B) and i5 (C).
Figure 2B:
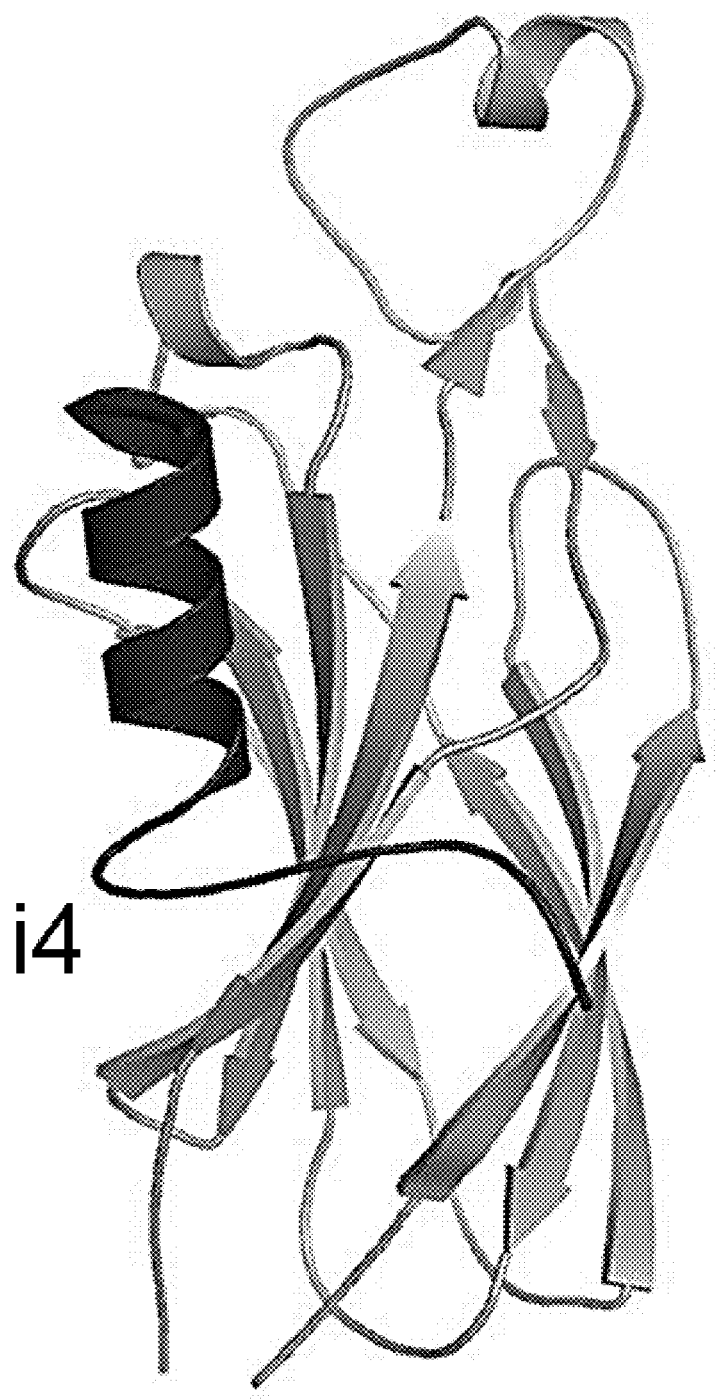
Figure 2C:
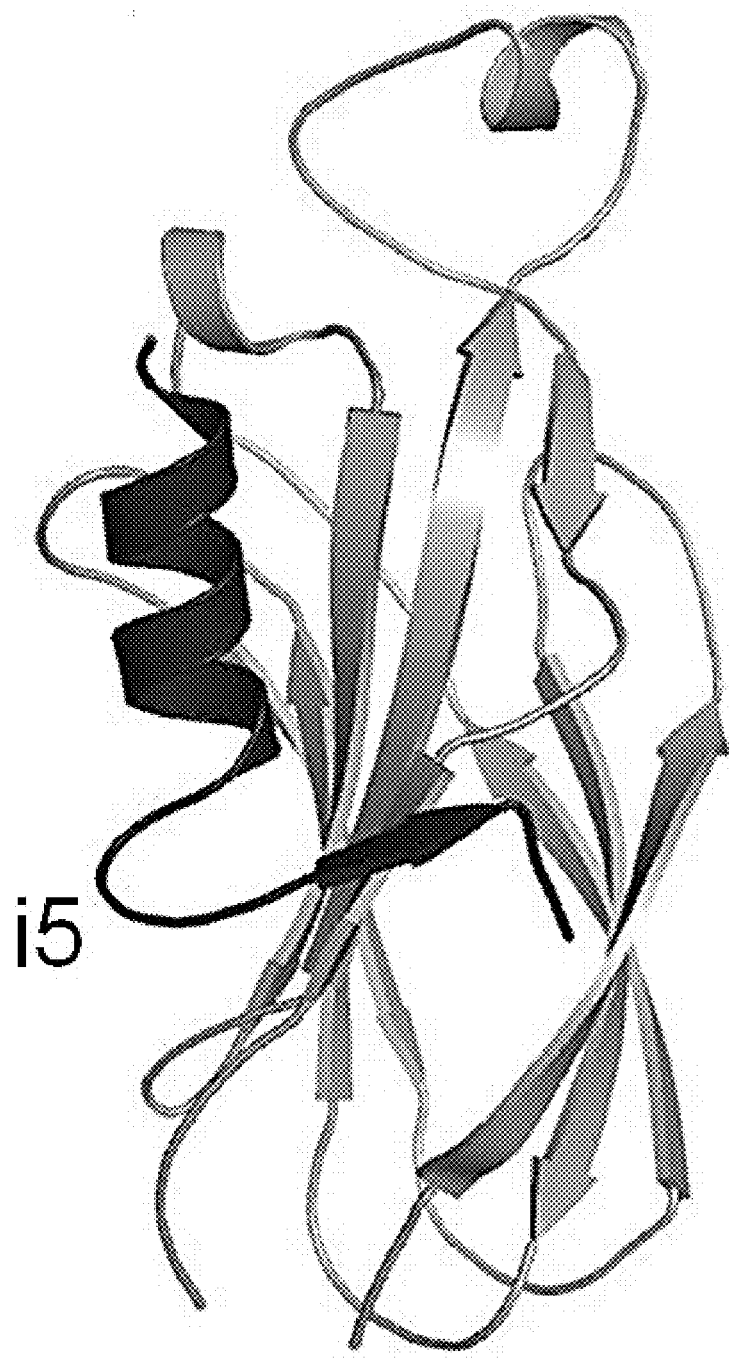

These different stages of design have increased the affinity of peptides for Asf1 by a factor of 200: starting from a fragment of histone H3 alone (peptide i1) displaying an affinity of 8 an inhibitor i4 (SEQ ID NO: 42) was obtained, which has an affinity of 180 nM 40 nM for which the inventors have resolved the structure of the complex with Asf1 at high resolution (FIG. 2). Another peptide, i5 (SEQ ID NO: 32), could then be designed, having an affinity of 40 nM±13 nM (FIG. 1). From this peptide, a control peptide was designed (i5mut, SEQ ID NO: 68). It has 90% identity with peptide i5, but is mutated to alanine on three key residues and no longer binds to Asf1. This peptide was synthesized to serve as a negative control in competition assays and interaction test. The sequence of peptide i5 was then optimized to obtain peptides i5_s3 (SEQ ID NO: 75), i5_D (SEQ ID NO: 76), i5_loopR (SEQ ID NO: 77), i5_loopA (SEQ ID NO: 78), i5_Aloop (SEQ ID NO: 79) and i6 (SEQ ID NO: 80) whose affinity is at least as good as that of peptide i5.

Biophysical and Structural Characterization:

The design of the peptides was achieved by several iterations between the biophysical characterization of the binding properties of the peptide and molecular modeling. The impact of mutations on the structure was systematically checked by circular dichroism and NMR. The three-dimensional structures of peptides i4 and i5 interacting with Asf1(1-156) were resolved by X-ray crystallography (FIG. 2).

Figure 3:
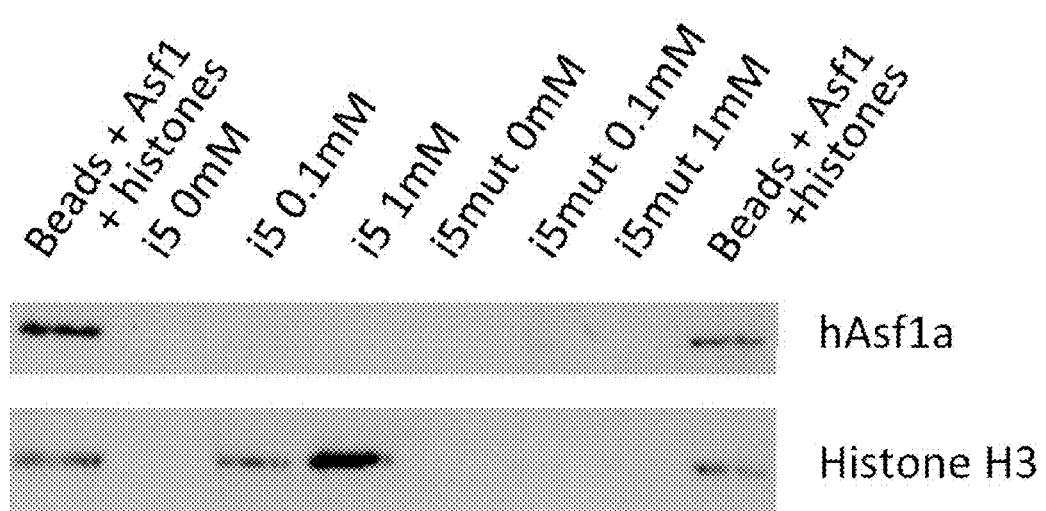
FIG. 3: Western blot analysis of competition assay on GST column of the Asf1-H3-H4 interaction by i5 (or i5mut), revealed by anti-Asf1 (hAsf1a) and anti-Histone H3 antibody.

Peptide/Histone Competition In Vitro:

The inventors have checked that the inhibitor peptide is capable of competing with histones for binding to Asf1 by competition assays on a GST column. To do this, GST beads linked to Asf1 were incubated with an excess of histones H3-H4, then washed and incubated with increasing concentrations of peptide. The eluted histones were analyzed by Western blot. When the beads were incubated with buffer only (0 mM i5 in FIG. 3) or with i5mut peptide (i5mut 0.1 and 1 mM in FIG. 3), the histones remain bound to Asf1. On the other hand, when beads were incubated with 0.1 mM, then 1 mM peptide i5, it was observed that the histones detached from the beads (wells 0.1 mM i5 and 1 mM i5 in FIG. 3). This result shows that, in vitro, the peptide is capable of dissociating the interaction between Asf1 and histones.

Figure 8:
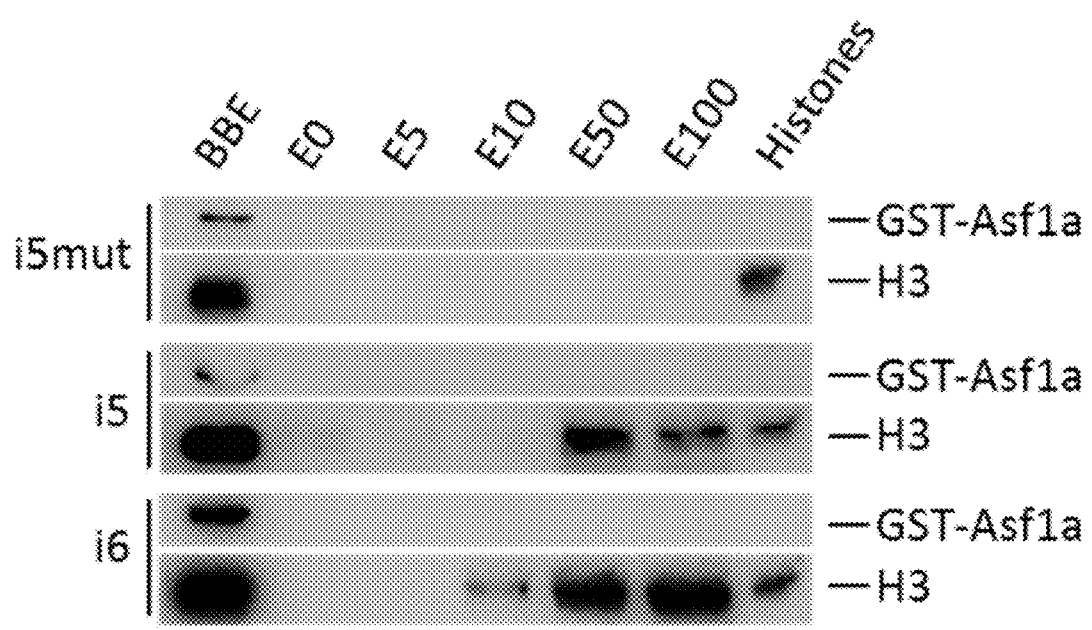
FIG. 8: Western blot analysis of competition assay on GST column of the interaction Asf1-H3-H4 by i5, i5mut, i6, revealed by anti-GST (GST-Asf1a) and anti-histone H3 antibody. E0: no peptide, E5: 5 µM, E10: 10 µM, E50: 50 µM, E100: 100 µM.

When the same experiment was carried out with different amounts of peptides i5 and i6 and the control peptide i5mut (FIG. 8), it was observed that a smaller amount of peptide i6 was sufficient to dissociate the Asf1-histones complex.

Figure 4A:
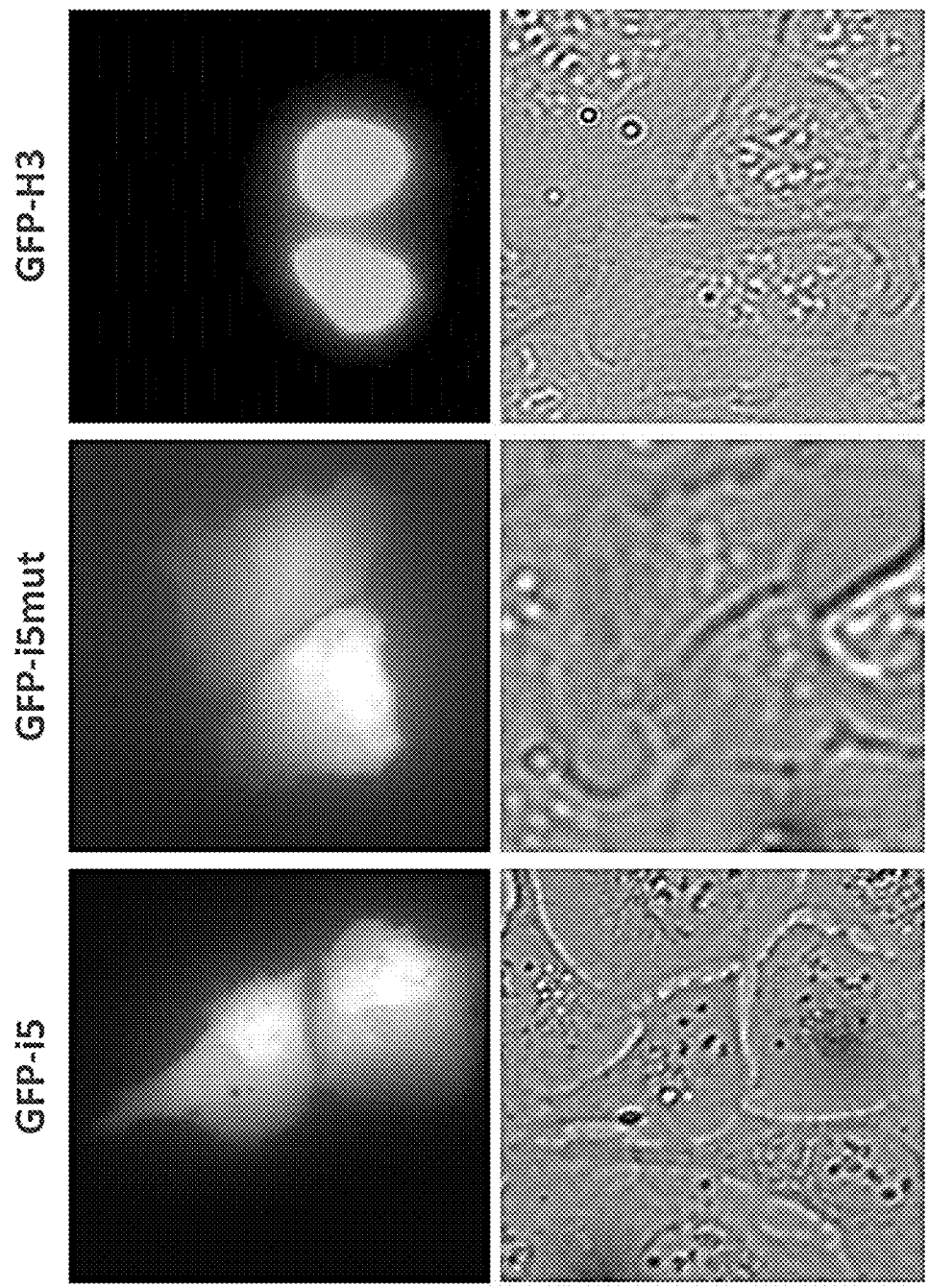
FIG. 4A: Visualization by fluorescence (top) and optical (bottom) microscopy of peptide i5, i5mut and GFP (Green fluorescent protein)-labeled whole histone H3 in human U2OS cells.
Figure 4B:
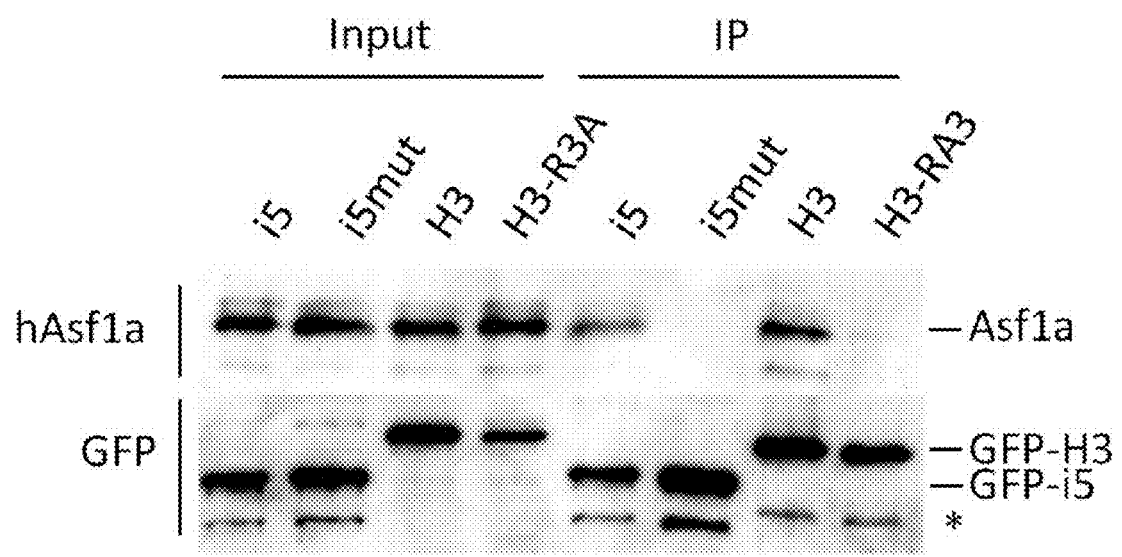
FIG. 4B: Co-immunoprecipitation of Asf1 with whole histone H3, mutant histone (H3-R3A) and with peptide i5 and i5mut, revealed by anti-Asf1 (hAsf1a) and anti-GFP antibody. Asterisk indicates the presence of degradation products (GFP alone).

Characterization of the Asf1-Peptide Interaction In Vivo:

The inventors checked that the interaction between Asf1 and the peptides can be established in human cells by co-immunoprecipitation (FIG. 4). To do this, U2OS cells were transfected using Lipofectamine (Invitrogen) with plasmids harboring the gene for peptides i5 and i5mut, capable (or not, respectively) of binding Asf1, in the form of a fusion protein with the eGFP fluorescent protein in order to control the location of the peptide by fluorescence microscopy. The location of the fusion proteins was analyzed by fluorescence microscopy (FIG. 4A). The positive control was cells transfected with full histone H3 also fused to eGFP, while a second negative control consisted of cells transfected with histone H3 mutated on three key residues so as not to interact with Asf1 (H3-R3A). In this system, a co-immunoprecipitation with Asf1 was observed as expected (FIG. 4B).

Characterization of the Phenotype Related to the Addition of the Peptide in Human Cells:

To analyze the biological effect of the peptide in cultured cells, the inventors tested at the same time its capacity to penetrate into cells. The peptide was vectorized using a short sequence of about 10 amino acids at the N-terminal that confers a "Cell Penetrating Peptide" property to the peptide, that is to say the capacity of being internalized in cells by a mechanism known as transduction. This sequence $(RRP)_5$ has been published by the Schepartz group in 2007 (Journal of the American Chemical Society 129(47): 14578).

Figure 5:
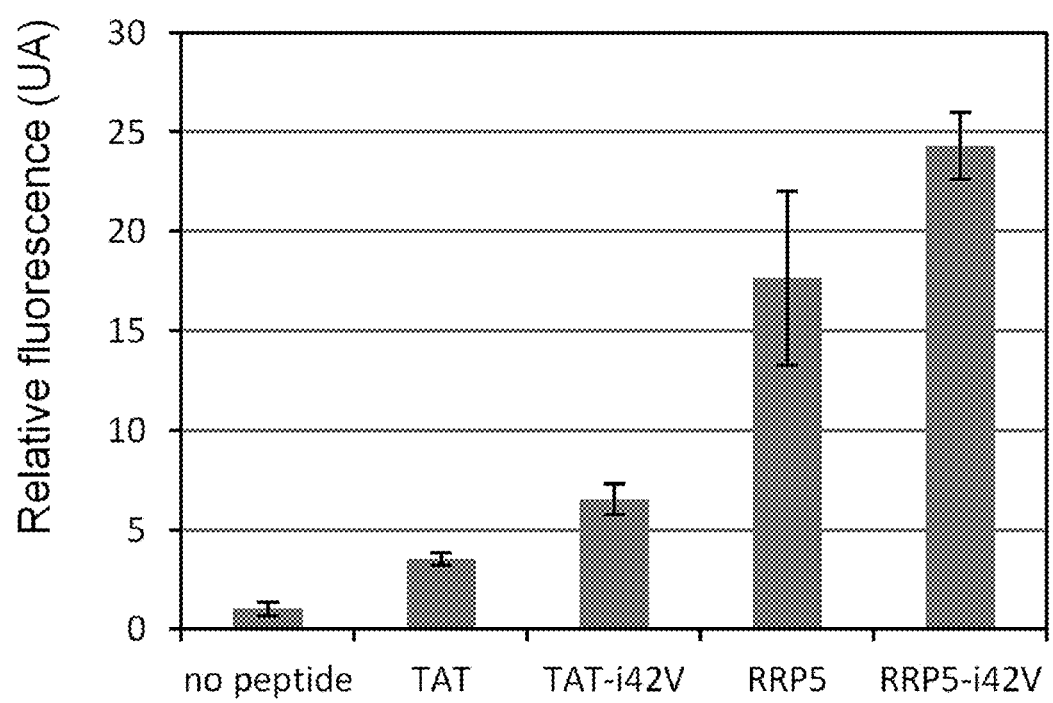
FIG. 5: Analysis of the penetration of peptides (carrying FITC) into U2OS cells by flow cytometry.

The capacity of the peptide i42V (SEQ ID NO: 47) coupled either to the sequence TAT (peptide TAT-i42V, SEQ ID NO: 58) or to the sequence $(RRP)_5$ (peptide RRP5-i42V, SEQ ID NO 59) was measured using these peptides coupled to an FITC label. The mean fluorescence of the cells was analyzed by flow cytometry (FIG. 5). Interestingly, the peptides coupled to the penetration sequences penetrate more effectively than the penetration sequences alone.

Figure 6:
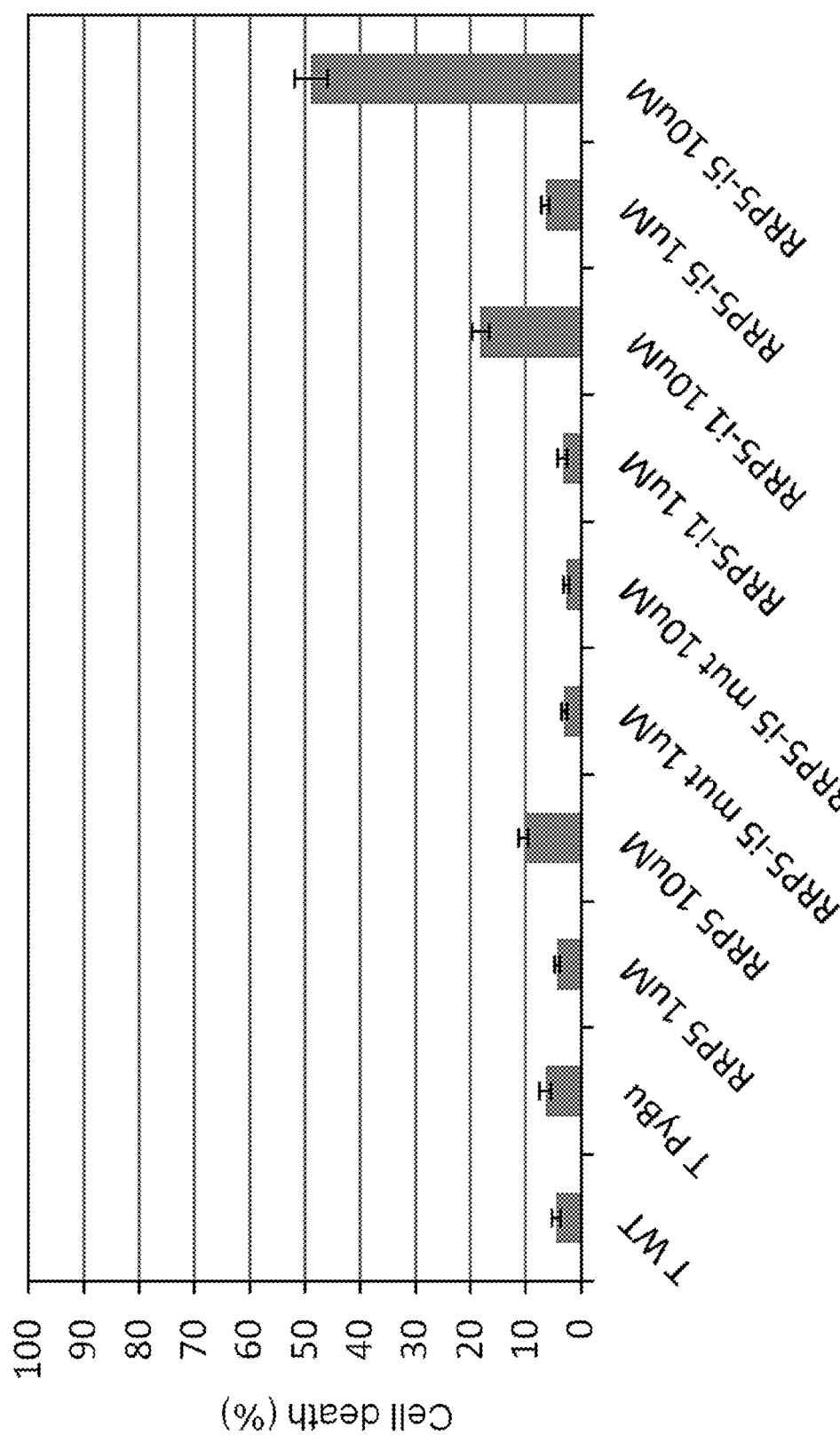
FIG. 6: Toxicity at 24 hours on U2OS cells transduced with different peptides, without peptide (T WT), in the presence of pyrene butyrate (T PyBu), and in the presence of pyrene butyrate and the peptide at the indicated concentration.
Figure 10:
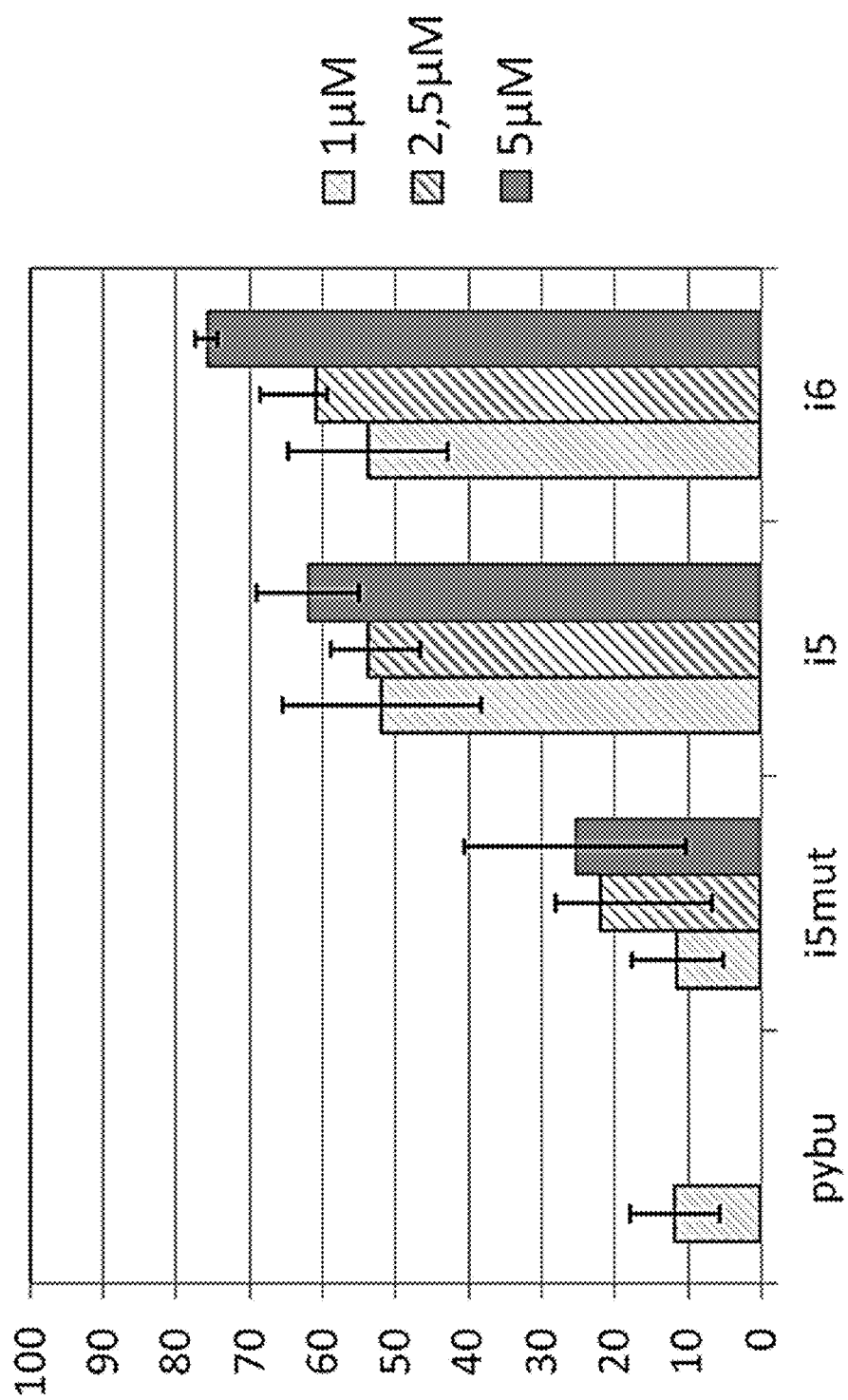
FIG. 10: Measurement of cell toxicity (MTT assay) of peptides i5mut, i5, and i6, 48H after transfection into HeLa cells in the form of a peptide fused with the sequence $(RRP)_5$.

To optimize the internalization of the peptide, the transduction was performed in the presence of pyrene butyrate, according to the method proposed by Takeuchi et al. (ACS CHEMICAL BIOLOGY, 2006. 1(5): p. 299-303). Peptides with different affinities for Asf1 were transduced, as well as a control peptide which does not bind to Asf1 because of three mutations on residues that are crucial for the interaction with Asf1 (i5mut, SEQ ID NO: 68) in U2OS cells. Remarkably, 24 hours after transduction of the highest affinity peptide at a concentration of 10 µM, 30% mortality was observed whereas no toxicity was seen for control cells treated either with pyrene butyrate alone or with peptide RRP5-i5mut which does not bind to Asf1. Furthermore, this toxicity was correlated with the affinity of the peptides initially measured by microcalorimetry, which strongly suggests that the observed toxicity is indeed related to inhibition of the Asf1 chaperone protein (FIG. 6). RRP5-i1 is the peptide of SEQ ID NO: 60. RRP5-i5 is the peptide of SEQ ID NO: 66. This correlation between the affinity of the peptide for Asf1 and the induced cell toxicity was confirmed for another cell type (HeLa cells) and by using another protocol to measure cell survival, the MTT assay (FIG. 10).

Figure 9:
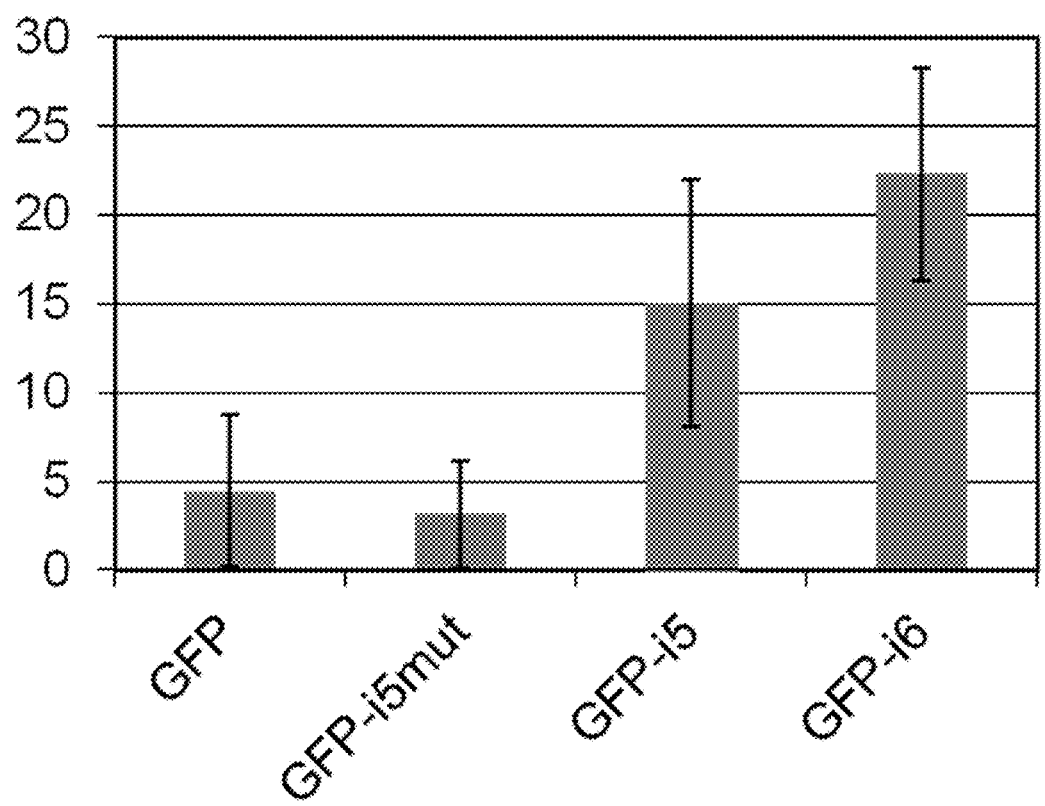
FIG. 9: Measurement of cell toxicity (MTT assay) of peptides i5mut, i5 and i6, 48 hours after transfection into U2OS cells in the form of a plasmid coding for a GFP-peptide fusion protein.

To verify that this toxicity was not an artifact related to the way the peptide was introduced into the cell, the inventors introduced the peptide as a plasmid by transfection (nucleofection). They also observed a correlation between the affinity of the peptide for Asf1 in vitro and cell toxicity (FIG. 9).

Figure 7:
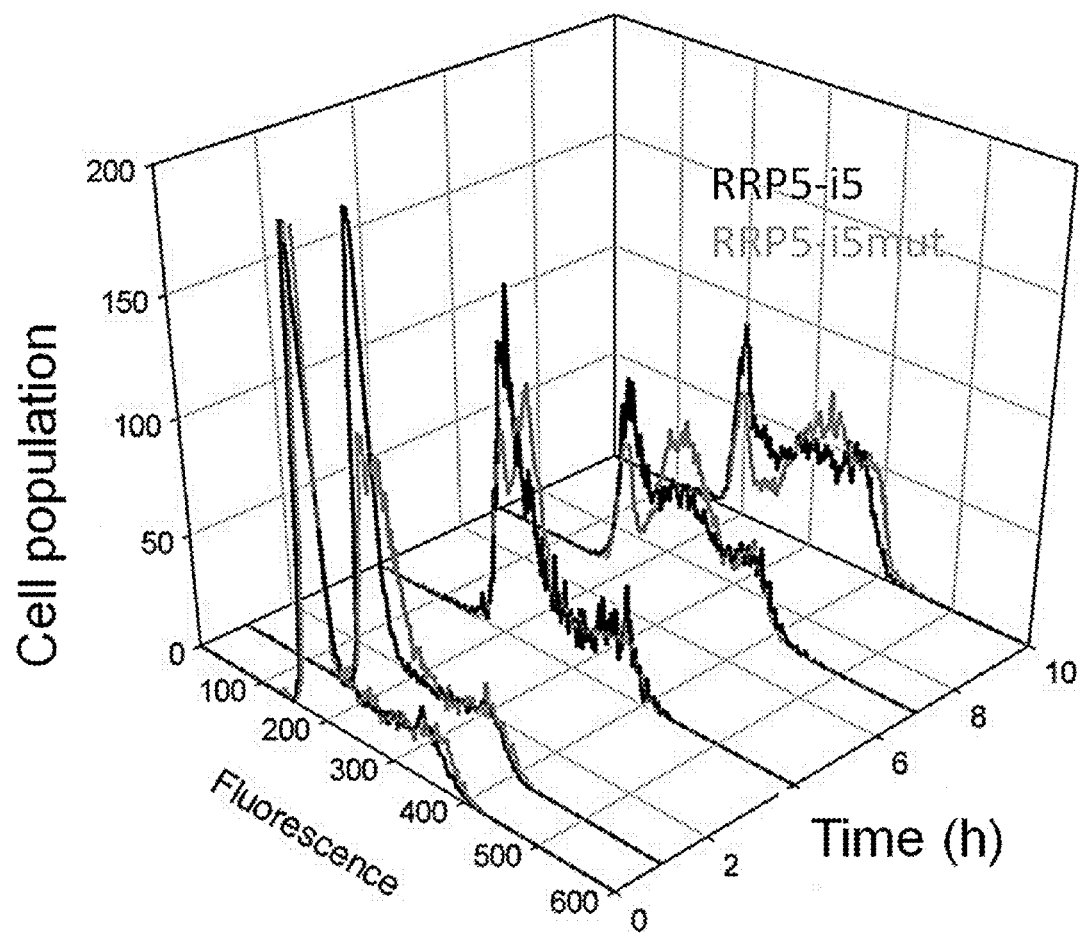
FIG. 7: Disruption of cell cycle progression by the action of peptide i5 or i5mut.

As cell toxicity can result from a number of very different reasons, the inventors sought to highlight a phenotype more specifically related to inhibition of the Asf1 histone chaperone. For this they analyzed the effect of the transduction of the peptides on cell cycle progression. U2OS cells were synchronized in G1 phase. After restarting the cycle and transducing the peptides RRP5-i5 (SEQ ID NO: 66) or RRP5-i5mut (SEQ ID NO: 69) it was found that the transition between the G1 and S phases was slowed for the active version of the peptide and not its mutated version (FIG. 7), demonstrating the specificity of action of the peptide inhibitor of the Asf1-histone interaction.

Materials and Methods

Expression and Cloning

Human Asf1a and b proteins and the conserved N-terminal domain (1-156) of each of the isoforms were cloned into the vector peTM30. The unlabeled and $^{15}N$ and $^{13}C/^{15}N$ labeled recombinant proteins were purified according to the protocol of Mousson et al. (2004, Journal of Biomolecular NMR, 29(3): 413-414). The peptides were either produced by chemical synthesis (GENECUST), or cloned after gene synthesis (GENECUST) in the vector Gateway pDest 17 (Invitrogen), then purified according to the protocol of Mousson et al. (2005, Proc. Natl. Sci. USA, 102(17): p. 5975-5980).

Design

The peptides were designed using the software Rosetta (Das et al., 2008, Annual Review of Biochemistry, 77: p. 363-382), Fold-X (Guerois et al., 2002, J Mol Biol 320(2): 369-387) and AGADIR (Lacroix, et al., 1998, J Mol Biol 284(1): 173-191).

Circular Dichroism

Circular dichroism experiments were performed on a Jasco apparatus using a peptide concentration of 50 µM, in $H_2O$ at pH 5.5, at 5° C.

Calorimetry

All calorimetry experiments were carried out in 50 mM Tris buffer pH 7.4 at 5° C., unless otherwise indicated. Peptides were introduced in the syringe at a concentration of 0.5 or 0.16 and Asf1 was added to the cuvette at a concentration of 30 µM or 10 µM. Calorimetry tests were also conducted at 25° C. or in 50 mM Tris buffer, 150 mM NaCl, pH 7.4 to obtain more detailed information on the characteristics of the interactions studied.

NMR

All NMR samples were prepared in either a buffer of $H_2O$, 10% $D_2O$, 0.1% $NaN_3$, 1 mM EDTA, 0.1% $NaN_3$, 0.1 mM 2,2-dimethyl-2-silapentane-5-sulfonate, pH 5.5 for NMR spectra of the peptides alone, or in 10 mM Tris $D_{11}$ buffer containing 0.1% $NaN_3$, 1 mM EDTA, 0.1 mM 2,2-dimethyl-2-silapentane-5-sulfonate, 10% $D_2O$, pH 7.4. Several types of samples were used: Asf1a 1-156 uniformly labeled with $^{15}N$ or $^{13}C/^{15}N$, complexed with unlabeled peptides. For these experiments, the sample concentration was 0.1 mM. NMR experiments were carried out on Bruker 600 or 700 MHz spectrometers equipped with cryoprobes.

Crystallography

Asf1 crystals complexed with inhibitor peptide i4 (SEQ ID NO: 60) were obtained by vapor diffusion in a solution of 100 mM Tris/HCl pH 7.5, 5% PEG 8000, 30% glycerol.

Those complexed with inhibitor peptide i5 (SEQ ID NO: 66) were obtained in conditions of 250 mM $LiSO_4$, 7% PEG 8000, 100 mM citric acid, pH 2.5, 22.5% xylitol.

The structure of the complexes was resolved by molecular replacement using the crystallographic structure of Asf1a (Pdb code 2io5).

Competition Assay on GST Column

The human protein GST-Asf1 1-156 was produced and then incubated with GST beads (glutathione S transferase, Sigma). For each experiment, 40 µg of recombinant Asf1 fixed to agarose beads were incubated with 400 µg of histones. After washing with 50 mM Tris buffer, pH 8, 150 mM NaCl, 1 mM EDTA, 1 mM DTT, 0.5% NP40, the beads were incubated with different concentrations of peptide (0 to 1 mM) dissolved in the same buffer. The amount of dissociated histones was revealed by Western blot with anti-GST and anti-H3 antibodies (AbCam).

Co-Immunoprecipitation

U2OS cells were transfected with plasmids harboring histones or the peptide, tagged with EYFP. 24 hours later the cells were lysed, then incubated on beads comprising an anti-GFP antibody (Miltenyi Biotec). After washing in 100 mM potassium acetate buffer, 30 mM KCl, 10 mM $NaH_2PO_4$, 1 mM $MgCl_2$, 0.2% Triton X100, 200 mM NaCl, proteins fixed to the beads were analyzed by Western blot with anti-GFP (AbCam) and anti-Asf1 (produced by the group of Carl Mann) antibodies.

Cell Penetration Test

U2OS cells were incubated with culture medium supplemented with fluorescent peptide at a final concentration of 1 µM for 1 hour, then washed with PBS buffer and detached by addition of trypsin, washed with PBS buffer, then analyzed by flow cytometry (FACS).

Toxicity Tests and Phenotypes

To test the phenotypes induced by the peptide, a newly developed protocol for the "Cell Penetrating TAT" was used. The peptides were dissolved in PBS buffer containing 50 pyrene butyrate and incubated with U2OS (or HeLa) cells for 4 minutes. Cells were then washed three times with PBS buffer, then taken up in culture medium containing fetal calf serum. Cell death was analyzed by FACS 24 to 48 hours later by propidium iodide incorporation or by an MTT assay (3-(4,5-dimethylthiazol-2-yl)-2,5-diphenyl tetrazolium bromide). (Mosmann, T. J. Immunol. Methods 65: 55-63, 1983).

Nucleofection

U2OS cells were transfected with a vector carrying the gene coding for the inhibitor peptides in the form of a GFP fusion protein using a nucleofection protocol (NUCELO-FACTOR Solution V, Lonza) according to the supplier's protocol.

Cell Cycle Disruption Test

U2OS cells were synchronized in G1 phase by overnight incubation in mimosine (200 The cycle was restarted by a PBS wash. Peptides dissolved in PBS buffer containing 50 pyrene butyrate were then incubated with the cells for 4 minutes, the cells washed three times with PBS buffer and then taken up in culture medium containing fetal calf serum. Cells were harvested 1 hour, 4 hours, 7 hours and 10 hours later. The medium was removed and the cell pellet was taken up in 500 µL of PBS+40 µg/mL PI (propidium iodide)+40 µg/mL RNAse. After incubation for 20 minutes at 4° C., the fluorescence of the cells was analyzed by flow cytometry (FACS).

Tablet of sequence listings

| SEQ ID No | Description |
| --- | --- |
| 1 | E1 of formula (I), mode a1) |
| 2 | E1 of formula (I), mode a2) |
| 3 | B of formula (II) |
| 4 | E2 of formula (III) |
| 5 | E1-B-E2 of formula (IV) |
| 6 | E1-B-E2 of formula (V) |
| 7 | E1 of formula (I), mode a1) |
| 8 | E1 of formula (I), mode a2) |
| 9 | E1-B-E2 of formula (VI) |
| 10 | E1-B-E2 of formula (VII) |
| 11 | E1-B-E2 of formula (VIII) |
| 12 | E1-B-E2 of formula (IX) |
| 13 | element E1-B-E2 |
| 14 | element E1-B-E2 |
| 15 | element E1-B-E2 |
| 16 | element E1-B-E2 |
| 17 | element E1-B-E2 |
| 18 | element E1-B-E2 |
| 19 | element E1-B-E2 |
| 20 | element E1-B-E2 |
| 21 | element E1-B-E2 |
| 22 | element E1-B-E2 |
| 23 | element E1-B-E2 |
| 24 | element E1-B-E2 |
| 25 | element E1-B-E2 |
| 26 | element E1-B-E2 |
| 27 | element E1-B-E2 |
| 28 | element E1-B-E2 |
| 29 | element E1-B-E2 |
| 30 | element E1-B-E2 |
| 31 | element E1-B-E2 |
| 32 | element E1-B-E2 - peptide i5 |
| 33 | element E1-B-E2 |
| 34 | TAT peptide |
| 35 | penetratin |
| 36 | poly-arginine |
| 37 | (RRP)$_5$ |
| 38 | inhibitor peptide Asf1/H3-H4-peptide i4_1 |
| 39 | inhibitor peptide Asf1/H3-H4 |
| 40 | inhibitor peptide Asf1/H3-H4-peptide i4_2 |
| 41 | inhibitor peptide Asf1/H3-H4 |
| 42 | inhibitor peptide Asf1/H3-H4- peptide i4 |
| 43 | inhibitor peptide Asf1/H3-H4 |
| 44 | inhibitor peptide Asf1/H3-H4 |
| 45 | inhibitor peptide Asf1/H3-H4 |
| 46 | inhibitor peptide Asf1/H3-H4 |
| 47 | inhibitor peptide Asf1/H3-H4-peptide i42V |
| 48 | inhibitor peptide Asf1/H3-H4-peptide i4V |
| 49 | inhibitor peptide Asf1/H3-H4 |
| 50 | inhibitor peptide Asf1/H3-H4-peptide RRP5-i42V-CA |
| 51 | inhibitor peptide Asf1/H3-H4 |
| 52 | inhibitor peptide Asf1/H3-H4 |
| 53 | inhibitor peptide Asf1/H3-H4 |
| 54 | inhibitor peptide Asf1/H3-H4 |
| 55 | inhibitor peptide Asf1/H3-H4 |
| 56 | inhibitor peptide Asf1/H3-H4 |
| 57 | inhibitor peptide Asf1/H3-H4 |
| 58 | inhibitor peptide Asf1/H3-H4-peptide TAT-i42V |
| 59 | inhibitor peptide Asf1/H3-H4-peptide RRP5-i42V |
| 60 | inhibitor peptide Asf1/H3-H4-peptide RRP5-i1 |
| 61 | inhibitor peptide Asf1/H3-H4 |
| 62 | inhibitor peptide Asf1/H3-H4 |
| 63 | inhibitor peptide Asf1/H3-H4 |
| 64 | inhibitor peptide Asf1/H3-H4 |
| 65 | inhibitor peptide Asf1/H3-H4 |
| 66 | inhibitor peptide Asf1/H3-H4-peptide RRP5-i5 |
| 67 | inhibitor peptide Asf1/H3-H4 |
| 68 | Peptide i5mut |
| 69 | Peptide RRP5-i5mut |
| 70 | Peptide i1 |
| 71 | Stabilized H3 fragment |
| 72 | Stabilized H3 fragment |
| 73 | inhibitor peptide Asf1/H3-H4 |
| 74 | inhibitor peptide Asf1/H3-H4 |
| 75 | Peptide i5_s3 |
| 76 | Peptide i5_D |
| 77 | Peptide i5_loopR |
| 78 | Peptide i5_loopA |
| 79 | Peptide i5_Aloop |
| 80 | Peptide i6 |
| 81 | Peptide RRP5-i6 |
| 82 | E1-B-E2 of formula (X) |

The invention claimed is:

1. A peptide comprising elements E1-B-E2, wherein:
  a) E1 is a peptide characterized by the sequence of formula (I)

$$X_1\text{-}X_2\text{-}X_3\text{-}X_4\text{-}X_5\text{-}K\text{-}X_6\text{-}X_7\text{-}X_8\text{-}L\text{-}X_9\text{-}X_{10}\text{-}R\text{-}I\text{-}X_{11} \quad (I)$$

wherein the peptide of formula (I) is either:
  i) SEQ ID NO: 1 wherein
  $X_1$ and $X_2$ are absent;
  $X_3$ is an amino acid selected from the group consisting of A, C, V, P, L, I, M, F, W, R and Y;
  $X_4$ is an amino acid selected from the group consisting of T, S, P, D, M and N;
  $X_5$ is an amino acid selected from A, R, D, N, C, G, Q, E, H, I, L, K, M, F, P, S, T, V, W and Y;
  $X_6$ is an amino acid selected from the group consisting of Q, E, L, M, A, D, and W;
  $X_7$, $X_8$ and $X_9$, independently of each other, are an amino acid selected from A, R, D, N, C, G, Q, E, H, I, L, K, M, F, P, S, T, V, W and Y, provided that at least two of the residues $X_7$, $X_8$ and $X_9$ are an amino acid selected from the group consisting of A, R, D, N, C, G, Q, E, H, L, K, M, F, S, W and Y; and
  $X_{10}$ and $X_{11}$, independently of each other, are an amino acid selected from A, R, D, N, C, G, Q, E, H, I, L, K, M, F, P, S, T, V, W and Y; or
  ii) SEQ ID NO: 2 wherein
  $X_1$ is absent or is an amino acid selected from A, R, D, N, C, G, Q, E, H, I, L, K, M, F, P, S, T, V, W and Y;
  $X_2$ is absent or is an amino acid selected from A, R, D, N, C, G, Q, E, H, I, L, K, M, F, P, S, T, V, W and Y;
  $X_3$ is an amino acid selected from the group consisting of T, S, P, D and N;
  $X_4$ and $X_5$, independently of each other, are an amino acid selected from the group consisting of A, R, D, N, C, G, Q, E, H, L, K, M, F, S, W and Y;
  $X_6$ is an amino acid selected from the group consisting of Q, E, L, M, A, D and W;
  $X_7$, $X_8$ and $X_9$, independently of each other, are an amino acid selected from the amino acids A, R, D, N, C, G, Q, E, H, I, L, K, M, F, P, S, T, V, W and Y, provided that at least two of the residues $X_7$, $X_8$ and $X_9$ are an amino acid selected from the group consisting of A, R, D, N, C, G, Q, E, H, L, K, M, F, S, W and Y; and
  $X_{10}$ and $X_{11}$, independently of each other, are an amino acid selected from A, R, D, N, C, G, Q, E, H, I, L, K, M, F, P, S, T, V, W and Y;
  b) B is a peptide characterized by the sequence of formula (II)

$$G\text{-}X_{12}\text{-}G\text{-}X_{13}\text{-}X_{14} \quad (II) \text{ (SEQ ID NO: 3)}$$

wherein:
  $X_{12}$ is an amino acid selected from A, R, D, N, C, G, Q, E, H, I, L, K, M, F, P, S, T, V, W and Y;
  $X_{13}$ is absent or selected from the amino acids G, A and S; and
  $X_{14}$ is absent or is an amino acid selected from A, R, D, N, C, G, Q, E, H, I, L, K, M, F, P, S, T, V, W and Y; and
  c) E2 is a peptide characterized by the sequence of formula (III)

$$X_{15}\text{-}X_{16}\text{-}X_{17}\text{-}X_{18}\text{-}G\text{-}X_{19}\text{-}X_{20} \quad (III) \text{ (SEQ ID NO: 4)}$$

wherein:
  $X_{15}$ is an amino acid selected from A, R, D, N, C, G, Q, E, H, I, L, K, M, F, P, S, T, V, W and Y;
  $X_{16}$ is T or V;
  $X_{17}$ is an amino acid selected from A, R, D, N, C, G, Q, E, H, I, L, K, M, F, P, S, T, V, W and Y;
  $X_{18}$ is an amino acid selected from the group consisting of A, D, N, C, G, Q, E, H, I, L, M, F, P, S, T, V, W and Y;
  $X_{19}$ is an amino acid selected from the group consisting of A, C, V, P, L, I, M, F, W and Y; and
  $X_{20}$ is absent or is an amino acid selected from A, R, D, N, C, G, Q, E, H, I, L, K, M, F, P, S, T, V, W and Y.

2. The peptide according to claim 1, wherein element E1 is either:
  a) $X_1$ and $X_2$ are absent;
  $X_3$ is an amino acid selected from the group consisting of A, C, V, P, L, I, M, F, W and Y;
  $X_4$ is an amino acid selected from the group consisting of T, S, P, D and N; and
  $X_5$ is an amino acid selected from A, R, D, N, C, G, Q, E, H, I, L, K, M, F, P, S, T, V, W and Y;
  $X_6$ is an amino acid selected from the group consisting of Q, E, L, M, A, and W;
  $X_7$, $X_8$, and $X_9$, independently of each other, are an amino acid selected from the group consisting of A, R, D, N, C, G, Q, E, H, L, K, M, F, S, W and Y; and X₁₀ and X₁₁, independently of each other, are an amino acid selected from A, R, D, N, C, G, Q, E, H, I, L, K, M, F, P, S, T, V, W and Y;
or
b) X₁, X₂, X₁₀ and X₁₁, independently of each other, are an amino acid selected from A, R, D, N, C, G, Q, E, H, I, L, K, M, F, P, S, T, V, W and Y;
X₄ and X₅, independently of each other, are an amino acid selected from the group consisting of A, R, D, N, C, G, Q, E, H, L, K, M, F, S, W and Y;
X₃ is an amino acid selected from the group consisting of T, S, P, D and N;
X₆ is an amino acid selected from the group consisting of Q, E, L, M, A, and W;
X₇, X₈, and X₉, independently of each other, are an amino acid selected from the group consisting of A, R, D, N, C, G, Q, E, H, L, K, M, F, S, W and Y; and
the other residues being as defined in claim 1.

3. The peptide according to claim 1, wherein:
element E1 is either:
a) X₁ and X₂ are absent;
X₃ is I, R or L;
X₄ is T or M;
X₅ is P;
X₆ is E or D;
X₇ is selected from the group consisting of R, A, I and E;
X₈ is selected from the group consisting of R, Q and E;
X₉ is R or A;
X₁₀ is R; and
X₁₁ is R or E;
or
b) X₁, X₇ and X₉ are A;
X₂ is S;
X₃ is T;
X₄ is E or R;
X₆ is W;
X₈ is E; and
X₅, X₁₀ and X₁₁ are R;
and elements B and E2 are
X₁₂ is A or P;
X₁₃ is absent or selected from the amino acids G, A and S;
X₁₄ is absent or S;
X₁₅ is R or V;
X₁₆ is T or V;
X₁₇ is L;
X₁₈ is Y, N or D;
X₁₉ is selected from the group consisting of F, M, A and Q; and
X₂₀ is selected from the group consisting of G, Q and N.

4. The peptide according to claim 1, wherein the elements E1-B-E2 comprise:

(SEQ ID NO: 11)
X₃-X₄-P-K-X₆-X₇-X₈-L-X₉-R-R-I-X₁₁-G-X₁₂-G-X₁₃-X₁₄-X₁₅-X₁₆-L-X₁₈-G-X₁₉-X₂₀ (VIII)

wherein:
X₃ is I, R or L;
X₄ is T or M;
X₆ is E or D;
X₇ is selected from the group consisting of R, A, I and E;
X₈ is selected from the group consisting of R, Q and E;
X₉ is R or A;
X₁₁ is R or E;
X₁₂ is A or P;
X₁₃ is absent or selected from the amino acids G, A and S;
X₁₄ is absent or S;
X₁₅ is R or V;
X₁₆ is T or V;
X₁₈ is Y, N or D;
X₁₉ is F or M; and
X₂₀ is selected from the group consisting of G, Q and N;
or (SEQ ID NO: 12)
A-S-T-X₄-R-K-W-A-E-L-A-R-R-I-R-G-X₁₂-G-X₁₃-X₁₄-X₁₅-X₁₆-L-X₁₈-G-X₁₉-X₂₀ (IX)

wherein:
X₄ is E or R;
X₁₂ is A or P;
X₁₃ is absent or selected from the amino acids G, A and S;
X₁₄ is absent or S;
X₁₅ is R or V;
X₁₆ is T or V;
X₁₈ is Y, N or D;
X₁₉ is F or M; and
X₂₀ is selected from the group consisting of G, Q and N;
or (SEQ ID NO: 82)
A-S-T-X₄-X₅-K-W-A-E-L-A-X₈-R-I-X₁₁-G-X₁₂-G-X₁₃-X₁₄-X₁₅-X₁₆-L-X₁₈-G-X₁₉-X₂₀ (XI)

wherein:
X₄, X₅, X₈ are E or R;
X₁₁ is R or A;
X₁₂ is A or P;
X₁₃ is absent or selected from the amino acids G, A and S;
X₁₄ is absent or S;
X₁₅ is R, V or A;
X₁₆ is T or V;
X₁₈ is Y, N or D;
X₁₉ is F or M; and
X₂₀ is selected from the group consisting of G, Q and N.

5. The peptide according to claim 1, wherein the elements E1-B-E2 comprise:

(SEQ ID NO: 13)
IMPKDIQLARRIRGAGGRTLYGFG;

(SEQ ID NO: 14)
IMPKDIQLARRIRGAGASRTLYGFG;

(SEQ ID NO: 15)
ITPKEAQLARRIRGAGGRTLNGFG;

(SEQ ID NO: 16)
ITPKEAQLARRIRGAGASRTLNGFG;

(SEQ ID NO: 17)
LTPKEAELARRIRGAGGRTLNGFG;

(SEQ ID NO: 18)
LTPKEAELARRIRGAGASRTLNGFG;

(SEQ ID NO: 19)
ITPKEAQLARRIEGAGASVTLNGFG;

```
                                         (SEQ ID NO: 20)
LTPKEAELARRIEGAGASVTLNGFG;

(SEQ ID NO: 21)
ITPKEEQLRRRIEGAGASVTLNGFG;

(SEQ ID NO: 22)
ITPKEAQLARRIRGAGGVTLNGFG;

(SEQ ID NO: 23)
LTPKEAELARRIRGAGGVTLNGFG;

(SEQ ID NO: 24)
LTPKEAELARRIRGAGRTLNGFG;

(SEQ ID NO: 25)
LTPKEAELARRIRGAGGRTLNGFG;

(SEQ ID NO: 26)
LTPKEAELARRIRGAGASRTLNGFG;

(SEQ ID NO: 27)
RTPKERRLARRIRGAGGRTLNGFG;

(SEQ ID NO: 28)
RTPKEARLARRIRGAGGRTLNGFG;

(SEQ ID NO: 29)
LTPKEAELARRIRGAGGVTYDGFG;

(SEQ ID NO: 30)
LTPKEAELARRIRGAGGVTLNGAN;

(SEQ ID NO: 31)
STERKWAELARRIRGAGGVTLNGFG;

(SEQ ID NO: 32)
ASTERKWAELARRIRGAGGVTLNGFG;

(SEQ ID NO: 33)
ASTRRKWAELARRIRGAGGVTLNGFG;

(SEQ ID NO: 75)
ASTEEKWARLARRIRGAGGVTLNGFG;

(SEQ ID NO: 76)
ASTERKWAELARRIRGAGGVTLDGFG;

(SEQ ID NO: 77)
ASTERKWAELARRIRGAGGRTLNGFG;

(SEQ ID NO: 78)
ASTERKWAELARRIRGAGGATLNGFG;

(SEQ ID NO: 79)
ASTERKWAELARRIAGAGGVTLNGFG;
or (SEQ ID NO: 80)
ASTEEKWARLARRIAGAGGVTLDGFG.
```

6. The peptide according to claim 1, wherein the peptide further comprises a peptide facilitating cell penetration.

7. The peptide according to claim 6, wherein the peptide facilitating cell penetration is RRPRRPRRPRRPRRP (SEQ ID NO: 37).

8. The peptide according to claim 1, the peptide comprising:

```
                                         (SEQ ID NO: 38)
GAMGTIMPKDIQLARRIRGAGGRTLYGFG;

(SEQ ID NO: 39)
GAMGTIMPKDIQLARRIRGAGASRTLYGFG;

(SEQ ID NO: 40)
GAMGTITPKEAQLARRIRGAGGRTLNGFG;

(SEQ ID NO: 41)
GAMGTITPKEAQLARRIRGAGASRTLNGFG;

(SEQ ID NO: 42)
GAMGTLTPKEAELARRIRGAGGRTLNGFG;

(SEQ ID NO: 43)
GAMGTLTPKEAELARRIRGAGASRTLNGFG;

(SEQ ID NO: 44)
GAMGTITPKEAQLARRIEGAGASVTLNGFG;

(SEQ ID NO: 45)
GAMGTLTPKEAELARRIEGAGASVTLNGFG;

(SEQ ID NO: 46)
GAMGTITPKEEQLRRRIEGAGASVTLNGFG;

(SEQ ID NO: 47)
GAMGTITPKEAQLARRIRGAGGVTLNGFG;

(SEQ ID NO: 48)
GAMGTLTPKEAELARRIRGAGGVTLNGFG;

(SEQ ID NO: 49)
GAMGTLTPKEAELARRIRGAGRTLNGFG;

(SEQ ID NO: 51)
GAMGTLTPKEAELARRIRGAGASRTLNGFG;

(SEQ ID NO: 52)
GAMGLTAAEHAKRSTLTPKEAQLARRIRGAGGVTLNGFG;

(SEQ ID NO: 53)
LTAAEHAKRSTLTPKEAELARRIRGAGGVTLNGFG;

(SEQ ID NO: 54)
LTAAEHAKRSTLTPKEAQLARRIEGAGASVTLNGFG;

(SEQ ID NO: 55)
LTAAEHAKRSTLTPKEAELARRIEGAGASVTLNGFG;

(SEQ ID NO: 56)
GAMGTRTPKERRLARRIRGAGGRTLNGFG;

(SEQ ID NO: 57)
GAMGTRTPKEARLARRIRGAGGRTLNGFG;

(SEQ ID NO: 58)
GRKKRRQRRRGAMGTITPKEAQLARRIRGAGGVTLNGFG;

(SEQ ID NO: 59)
RRPRRPRRPRRPRRPGAMGTITPKEAQLARRIRGAGGVTLNGFG;

(SEQ ID NO: 61)
GAMGTLTPKEAELARRIRGAGGVTYDGFG;

(SEQ ID NO: 62)
GAMGTLTPKEAELARRIRGAGGVTLNGFGASTG;

(SEQ ID NO: 63)
GAMGTLTPKEAELARRIRGAGGVTLNGANFVSTG;

(SEQ ID NO: 64)
GAMGRVPPAVRKLGNSTERKWAELARRIRGAGGVTLNGFG;

(SEQ ID NO: 65)
GAMGRVPPAVRKLGNASTERKWAELARRIRGAGGVTLNGFG;

(SEQ ID NO: 32)
ASTERKWAELARRIRGAGGVTLNGFG;

(SEQ ID NO: 33)
ASTRRKWAELARRIRGAGGVTLNGFG;

(SEQ ID NO: 75)
ASTEEKWARLARRIRGAGGVTLNGFG;

(SEQ ID NO: 76)
ASTERKWAELARRIRGAGGVTLDGFG;
```

ASTERKWAELARRIRGAGGRTLNGFG; (SEQ ID NO: 77)

ASTERKWAELARRIRGAGGATLNGFG; (SEQ ID NO: 78)

ASTERKWAELARRIAGAGGVTLNGFG; (SEQ ID NO: 79)

ASTEEKWARLARRIAGAGGVTLDGFG; (SEQ ID NO: 80)

RRPRRPRRPRRPRRPASTERKWAELARRIRGAGGVTLNGFGGCA; (SEQ ID NO: 66)

RRPRRPRRPRRPRRPASTERKWAELARRIRGAGGVTLNGFG; (SEQ ID NO: 67)

RRPRRPRRPRRPRRPGAMGTITPKEAQLARRIRGAGGVTLNGFGCA; (SEQ ID NO: 50)
or

RRPRRPRRPRRPRRPASTEEKWARLARRIAGAGGVTLDGFG. (SEQ ID NO: 81)

9. The peptide according to claim 1, the peptide comprising:

RRPRRPRRPRRPRRPGAMGTITPKEAQLARRIRGAGGVTLNGFG; (SEQ ID NO: 59)

RRPRRPRRPRRPRRPASTERKWAELARRIRGAGGVTLNGFGGCA; (SEQ ID NO: 66)

RRPRRPRRPRRPRRPASTERKWAELARRIRGAGGVTLNGFG; (SEQ ID NO: 67)

RRPRRPRRPRRPRRPGAMGTITPKEAQLARRIRGAGGVTLNGFGCA; (SEQ ID NO: 50)
and

RRPRRPRRPRRPRRPASTEEKWARLARRIAGAGGVTLDGFG. (SEQ ID NO: 81)

10. A pharmaceutical composition comprising the peptide according to claim 1, and optionally an anticancer agent.

11. The peptide according to claim 1, the peptide consisting of:

GAMGTIMPKDIQLARRIRGAGGRTLYGFG; (SEQ ID NO: 38)

GAMGTIMPKDIQLARRIRGAGASRTLYGFG; (SEQ ID NO: 39)

GAMGTITPKEAQLARRIRGAGGRTLNGFG; (SEQ ID NO: 40)

GAMGTITPKEAQLARRIRGAGASRTLNGFG; (SEQ ID NO: 41)

GAMGTLTPKEAELARRIRGAGGRTLNGFG; (SEQ ID NO: 42)

GAMGTLTPKEAELARRIRGAGASRTLNGFG; (SEQ ID NO: 43)

GAMGTITPKEAQLARRIEGAGASVTLNGFG; (SEQ ID NO: 44)

GAMGTLTPKEAELARRIEGAGASVTLNGFG; (SEQ ID NO: 45)

GAMGTITPKEEQLRRRIEGAGASVTLNGFG; (SEQ ID NO: 46)

GAMGTITPKEAQLARRIRGAGGVTLNGFG; (SEQ ID NO: 47)

GAMGTLTPKEAELARRIRGAGGVTLNGFG; (SEQ ID NO: 48)

GAMGTLTPKEAELARRIRGAGRTLNGFG; (SEQ ID NO: 49)

GAMGTLTPKEAELARRIRGAGASRTLNGFG; (SEQ ID NO: 51)

GAMGLTAAEHAKRSTLTPKEAQLARRIRGAGGVTLNGFG; (SEQ ID NO: 52)

LTAAEHAKRSTLTPKEAELARRIRGAGGVTLNGFG; (SEQ ID NO: 53)

LTAAEHAKRSTLTPKEAQLARRIEGAGASVTLNGFG; (SEQ ID NO: 54)

LTAAEHAKRSTLTPKEAELARRIEGAGASVTLNGFG; (SEQ ID NO: 55)

GAMGTRTPKERRLARRIRGAGGRTLNGFG; (SEQ ID NO: 56)

GAMGTRTPKEARLARRIRGAGGRTLNGFG; (SEQ ID NO: 57)

GRKKRRQRRRGAMGTITPKEAQLARRIRGAGGVTLNGFG; (SEQ ID NO: 58)

RRPRRPRRPRRPRRPGAMGTITPKEAQLARRIRGAGGVTLNGFG; (SEQ ID NO: 59)

GAMGTLTPKEAELARRIRGAGGVTYDGFG; (SEQ ID NO: 61)

GAMGTLTPKEAELARRIRGAGGVTLNGFGASTG; (SEQ ID NO: 62)

GAMGTLTPKEAELARRIRGAGGVTLNGANFVSTG; (SEQ ID NO: 63)

GAMGRVPPAVRKLGNSTERKWAELARRIRGAGGVTLNGFG; (SEQ ID NO: 64)

GAMGRVPPAVRKLGNASTERKWAELARRIRGAGGVTLNGFG; (SEQ ID NO: 65)

ASTERKWAELARRIRGAGGVTLNGFG; (SEQ ID NO: 32)

ASTRRKWAELARRIRGAGGVTLNGFG; (SEQ ID NO: 33)

ASTEEKWARLARRIRGAGGVTLNGFG; (SEQ ID NO: 75)

ASTERKWAELARRIRGAGGVTLDGFG; (SEQ ID NO: 76)

ASTERKWAELARRIRGAGGRTLNGFG; (SEQ ID NO: 77)

ASTERKWAELARRIRGAGGATLNGFG; (SEQ ID NO: 78)

ASTERKWAELARRIAGAGGVTLNGFG; (SEQ ID NO: 79)

ASTEEKWARLARRIAGAGGVTLDGFG; (SEQ ID NO: 80)

RRPRRPRRPRRPRRPASTERKWAELARRIRGAGGVTLNGFGGCA; (SEQ ID NO: 66)

RRPRRPRRPRRPRRPASTERKWAELARRIRGAGGVTLNGFG; (SEQ ID NO: 67)

-continued

```
                                  (SEQ ID NO: 50)
RRPRRPRRPRRPRRPRRPGAMGTITPKEAQLARRIRGAGGVTLNGFGCA;
or (SEQ ID NO: 81)
RRPRRPRRPRRPRRPRRPASTEEKWARLARRIAGAGGVTLDGFG.
```

\* \* \* \* \*

SEQUENCE LISTING

```
<160> NUMBER OF SEQ ID NOS: 82

<210> SEQ ID NO 1
<211> LENGTH: 13
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X3, a hydrophobic amino acid or R,
      preferably A, C, V, P, L, I, M, F, W, R or Y
<220> FEATURE:
<221> NAME/KEY: MISC_FEATURE
<222> LOCATION: (2)..(2)
<223> OTHER INFORMATION: Xaa is X4, being T, S, P, D, M or N
```

```
<220> FEATURE:
<221> NAME/KEY: MISC_FEATURE
<222> LOCATION: (3)..(3)
<223> OTHER INFORMATION: Xaa is X5, any amino acid (A, R, D, N, C, G, Q,
      E, H, I, L, K, M, F, P, S, T, V, W or Y)
<220> FEATURE:
<221> NAME/KEY: MISC_FEATURE
<222> LOCATION: (5)..(5)
<223> OTHER INFORMATION: Xaa is X6, being Q, E, L, M, A, D or W
<220> FEATURE:
<221> NAME/KEY: MISC_FEATURE
<222> LOCATION: (6)..(7)
<223> OTHER INFORMATION: Xaa are X7 and X8, any amino acids (A, R, D, N,
      C, G, Q, E, H, I, L, K, M, F, P, S, T, V, W or Y)
<220> FEATURE:
<221> NAME/KEY: MISC_FEATURE
<222> LOCATION: (9)..(10)
<223> OTHER INFORMATION: Xaa are X9 and X10, any amino acids (A, R, D,
      N, C, G, Q, E, H, I, L, K, M, F, P, S, T, V, W or Y)
<220> FEATURE:
<221> NAME/KEY: MISC_FEATURE
<222> LOCATION: (13)..(13)
<223> OTHER INFORMATION: Xaa is X11, any amino acid (A, R, D, N, C, G,
      Q, E, H, I, L, K, M, F, P, S, T, V, W or Y)

<400> SEQUENCE: 1

Xaa Xaa Xaa Lys Xaa Xaa Xaa Leu Xaa Xaa Arg Ile Xaa
1               5                   10

<210> SEQ ID NO 2
<211> LENGTH: 15
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X1, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (2)..(2)
<223> OTHER INFORMATION: Xaa is X2, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (3)..(3)
<223> OTHER INFORMATION: Xaa is X3, being T, S, P, D or N
<220> FEATURE:
<221> NAME/KEY: MISC_FEATURE
<222> LOCATION: (4)..(5)
<223> OTHER INFORMATION: Xaa are X4 and X5, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (7)..(7)
<223> OTHER INFORMATION: Xaa is X6, being Q, E, L, M, A, D or W
<220> FEATURE:
<221> NAME/KEY: MISC_FEATURE
<222> LOCATION: (8)..(9)
<223> OTHER INFORMATION: Xaa are X7 and X8, being any amino acids (A, R,
      D, N, C, G, Q, E, H, I, L, K, M, F, P, S, T, V, W or Y)
<220> FEATURE:
<221> NAME/KEY: MISC_FEATURE
<222> LOCATION: (11)..(12)
<223> OTHER INFORMATION: Xaa are X9 and X10, being any amino acids (A,
      R, D, N, C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X11, being any amino acids (A, R, D, N,
      C, G, Q, E, H, I, L, K, M, F, P, S, T, V, W or Y)
```

```
<400> SEQUENCE: 2

Xaa Xaa Xaa Xaa Xaa Lys Xaa Xaa Xaa Leu Xaa Xaa Arg Ile Xaa
1               5                   10                  15

<210> SEQ ID NO 3
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is X12, being any amino acids (A, R, D, N,
      C, G, Q, E, H, I, L, K, M, F, P, S, T, V, W or Y)
<220> FEATURE:
<221> NAME/KEY: MISC_FEATURE
<222> LOCATION: (4)..(4)
<223> OTHER INFORMATION: Xaa is X13, being missing or being G, A or S
<220> FEATURE:
<221> NAME/KEY: MISC_FEATURE
<222> LOCATION: (5)..(5)
<223> OTHER INFORMATION: Xaa is X14, being missing or being any amino
      acids (A, R, D, N, C, G, Q, E, H, I, L, K, M, F, P, S, T, V, W or
      Y)

<400> SEQUENCE: 3

Gly Xaa Gly Xaa Xaa
1               5

<210> SEQ ID NO 4
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X15, being any amino acids (A, R, D, N,
      C, G, Q, E, H, I, L, K, M, F, P, S, T, V, W or Y)
<220> FEATURE:
<221> NAME/KEY: MISC_FEATURE
<222> LOCATION: (2)..(2)
<223> OTHER INFORMATION: Xaa is X16, being T or V
<220> FEATURE:
<221> NAME/KEY: MISC_FEATURE
<222> LOCATION: (3)..(3)
<223> OTHER INFORMATION: Xaa is X17, being any amino acids (A, R, D, N,
      C, G, Q, E, H, I, L, K, M, F, P, S, T, V, W or Y)
<220> FEATURE:
<221> NAME/KEY: MISC_FEATURE
<222> LOCATION: (4)..(4)
<223> OTHER INFORMATION: Xaa is X18, being any non-positively charged
      amino acid (A, D, N, C, G, Q, E, H, I, L, M, F, P, S, T, V, W or
      Y)
<220> FEATURE:
<221> NAME/KEY: MISC_FEATURE
<222> LOCATION: (6)..(6)
<223> OTHER INFORMATION: Xaa is X19, being a hydrophobic amino acid,
      preferably A, C, V, P, L, I, M, F, W or Y
<220> FEATURE:
<221> NAME/KEY: MISC_FEATURE
<222> LOCATION: (7)..(7)
<223> OTHER INFORMATION: Xaa is X20, being missing or being any amino
      acid (A, R, D, N, C, G, Q, E, H, I, L, K, M, F, P, S, T, V, W or
      Y)

<400> SEQUENCE: 4

Xaa Xaa Xaa Xaa Gly Xaa Xaa
1               5

<210> SEQ ID NO 5
```

```
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X3, being an amino acid selected from
      the group consisting of A, C, V, P, L, I, M, F, W, R or Y,
      preferably from the group consisting of A, C, V, P, L, I, M, F, W
      or Y
<220> FEATURE:
<221> NAME/KEY: MISC_FEATURE
<222> LOCATION: (2)..(2)
<223> OTHER INFORMATION: Xaa is X4, being T, S, P, D, M or N
<220> FEATURE:
<221> NAME/KEY: MISC_FEATURE
<222> LOCATION: (3)..(3)
<223> OTHER INFORMATION: Xaa is X5, being any amino acid (A, R, D, N, C,
      G, Q, E, H, I, L, K, M, F, P, S, T, V, W or Y)
<220> FEATURE:
<221> NAME/KEY: MISC_FEATURE
<222> LOCATION: (5)..(5)
<223> OTHER INFORMATION: Xaa is X6, being Q, E, L, M, A, D or W
<220> FEATURE:
<221> NAME/KEY: MISC_FEATURE
<222> LOCATION: (6)..(7)
<223> OTHER INFORMATION: Xaa are X7 or X8, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (9)..(10)
<223> OTHER INFORMATION: Xaa are X9 or X10, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (13)..(13)
<223> OTHER INFORMATION: Xaa is X11, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X12, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (17)..(17)
<223> OTHER INFORMATION: Xaa is X13, being missing or being selected
      from the group consisting of G, A et S
<220> FEATURE:
<221> NAME/KEY: MISC_FEATURE
<222> LOCATION: (18)..(18)
<223> OTHER INFORMATION: Xaa is X14, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (19)..(19)
<223> OTHER INFORMATION: Xaa is X15, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (20)..(20)
<223> OTHER INFORMATION: Xaa is X16, being T or V
<220> FEATURE:
<221> NAME/KEY: MISC_FEATURE
<222> LOCATION: (21)..(21)
<223> OTHER INFORMATION: Xaa is X17, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (22)..(22)
<223> OTHER INFORMATION: Xaa is X18, being any non-positively charged
      amino acid (A, D, N, C, G, Q, E, H, I, L, M, F, P, S, T, V, W or
      Y)
<220> FEATURE:
<221> NAME/KEY: MISC_FEATURE
<222> LOCATION: (24)..(24)
```

```
<223> OTHER INFORMATION: Xaa is X19, being a hydrophobic amino acid,
      preferably A, C, V, P, L, I, M, F, W or Y
<220> FEATURE:
<221> NAME/KEY: MISC_FEATURE
<222> LOCATION: (25)..(25)
<223> OTHER INFORMATION: Xaa is X20, being missing or being any amino
      acid (A, R, D, N, C, G, Q, E, H, I, L, K, M, F, P, S, T, V, W or
      Y)

<400> SEQUENCE: 5

Xaa Xaa Xaa Lys Xaa Xaa Xaa Leu Xaa Xaa Arg Ile Xaa Gly Xaa Gly
1               5                   10                  15

Xaa Xaa Xaa Xaa Xaa Xaa Gly Xaa Xaa
            20                  25

<210> SEQ ID NO 6
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X1, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (2)..(2)
<223> OTHER INFORMATION: Xaa is X2, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (3)..(3)
<223> OTHER INFORMATION: Xaa is X3, being T, S, P, D or N
<220> FEATURE:
<221> NAME/KEY: MISC_FEATURE
<222> LOCATION: (4)..(5)
<223> OTHER INFORMATION: Xaa are X4 and X5, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (7)..(7)
<223> OTHER INFORMATION: Xaa is X6, being Q, E, L, M, A, D or W
<220> FEATURE:
<221> NAME/KEY: MISC_FEATURE
<222> LOCATION: (8)..(9)
<223> OTHER INFORMATION: Xaa are X7 and X8, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (11)..(12)
<223> OTHER INFORMATION: Xaa are X9 and X10, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X11, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (17)..(17)
<223> OTHER INFORMATION: Xaa is X12, being any amino acid (A, R, D, N,
      C, G, Q, E, H, I, L, K, M, F, P, S, T, V, W and Y)
<220> FEATURE:
<221> NAME/KEY: MISC_FEATURE
<222> LOCATION: (19)..(19)
<223> OTHER INFORMATION: Xaa is X13, being missing or being G, A or S
<220> FEATURE:
<221> NAME/KEY: MISC_FEATURE
<222> LOCATION: (20)..(20)
<223> OTHER INFORMATION: Xaa is X14, being missing or being any amino
      acid (A, R, D, N, C, G, Q, E, H, I, L, K, M, F, P, S, T, V, W or
```

```
          Y)
<220> FEATURE:
<221> NAME/KEY: MISC_FEATURE
<222> LOCATION: (21)..(21)
<223> OTHER INFORMATION: Xaa is X15, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (22)..(22)
<223> OTHER INFORMATION: Xaa is X16, being T or V
<220> FEATURE:
<221> NAME/KEY: MISC_FEATURE
<222> LOCATION: (23)..(23)
<223> OTHER INFORMATION: Xaa is X17, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (24)..(24)
<223> OTHER INFORMATION: Xaa is X18, being any non-positively charged
      amino acid (A, D, N, C, G, Q, E, H, I, L, M, F, P, S, T, V, W or
      Y)
<220> FEATURE:
<221> NAME/KEY: MISC_FEATURE
<222> LOCATION: (26)..(26)
<223> OTHER INFORMATION: Xaa is X19, being a hydrophobic amino acid,
      preferably A, C, V, P, L, I, M, F, W or Y
<220> FEATURE:
<221> NAME/KEY: MISC_FEATURE
<222> LOCATION: (27)..(27)
<223> OTHER INFORMATION: Xaa is X20, being missing or being any amino
      acid (A, R, D, N, C, G, Q, E, H, I, L, K, M, F, P, S, T, V, W or
      Y)

<400> SEQUENCE: 6

Xaa Xaa Xaa Xaa Xaa Lys Xaa Xaa Xaa Leu Xaa Xaa Arg Ile Xaa Gly
1               5                   10                  15

Xaa Gly Xaa Xaa Xaa Xaa Xaa Xaa Gly Xaa Xaa
            20                  25

<210> SEQ ID NO 7
<211> LENGTH: 13
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X3, being a hydrophobic amino acid (A,
      C, V, P, L, I, M, F, W or Y)
<220> FEATURE:
<221> NAME/KEY: MISC_FEATURE
<222> LOCATION: (2)..(2)
<223> OTHER INFORMATION: Xaa is X4, being T, S, P, D or N
<220> FEATURE:
<221> NAME/KEY: MISC_FEATURE
<222> LOCATION: (3)..(3)
<223> OTHER INFORMATION: Xaa is X5, being any amino acid (A, R, D, N, C,
      G, Q, E, H, I, L, K, M, F, P, S, T, V, W or Y)
<220> FEATURE:
<221> NAME/KEY: MISC_FEATURE
<222> LOCATION: (5)..(5)
<223> OTHER INFORMATION: Xaa is X6, being Q, E, L, M, A, or W
<220> FEATURE:
<221> NAME/KEY: MISC_FEATURE
<222> LOCATION: (6)..(7)
<223> OTHER INFORMATION: Xaa are X7 and X8, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (9)..(9)
<223> OTHER INFORMATION: Xaa is X9, being amino acid favorable to an
      alpha helix secondary structure, preferably A, R, D, N, C, G, Q,
      E, H, L, K, M, F, S, W or Y
<220> FEATURE:
```

```
<221> NAME/KEY: MISC_FEATURE
<222> LOCATION: (10)..(10)
<223> OTHER INFORMATION: Xaa is X10, being any amino acid, (A, R, D, N,
      C, G, Q, E, H, I, L, K, M, F, P, S, T, V, W or Y)
<220> FEATURE:
<221> NAME/KEY: MISC_FEATURE
<222> LOCATION: (13)..(13)
<223> OTHER INFORMATION: Xaa is X11, being any amino acid, (A, R, D, N,
      C, G, Q, E, H, I, L, K, M, F, P, S, T, V, W or Y)

<400> SEQUENCE: 7

Xaa Xaa Xaa Lys Xaa Xaa Xaa Leu Xaa Xaa Arg Ile Xaa
1               5                   10

<210> SEQ ID NO 8
<211> LENGTH: 15
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa are X1 and X2, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (3)..(3)
<223> OTHER INFORMATION: Xaa  is X3, being T, S, P, D or N
<220> FEATURE:
<221> NAME/KEY: MISC_FEATURE
<222> LOCATION: (4)..(5)
<223> OTHER INFORMATION: Xaa are X4 and X5, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (7)..(7)
<223> OTHER INFORMATION: Xaa is X6, being Q, E, L, M, A, or W
<220> FEATURE:
<221> NAME/KEY: MISC_FEATURE
<222> LOCATION: (8)..(9)
<223> OTHER INFORMATION: Xaa are X7 and X8, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (11)..(11)
<223> OTHER INFORMATION: Xaa is X9, being an amino acid favorable to an
      alpha helix secondary structure, preferably A, R, D, N, C, G, Q,
      E, H, L, K, M, F, S, W or Y
<220> FEATURE:
<221> NAME/KEY: MISC_FEATURE
<222> LOCATION: (12)..(12)
<223> OTHER INFORMATION: Xaa is X10, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X11, being any amino acid (A, R, D, N,
      C, G, Q, E, H, I, L, K, M, F, P, S, T, V, W or Y)

<400> SEQUENCE: 8

Xaa Xaa Xaa Xaa Xaa Lys Xaa Xaa Xaa Leu Xaa Xaa Arg Ile Xaa
1               5                   10                  15

<210> SEQ ID NO 9
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
```

```
<223> OTHER INFORMATION: Xaa is X3, being a hydrophobic amino acid
      selected from the group consisting of A, C, V, P, L, I, M, F, W
      and Y
<220> FEATURE:
<221> NAME/KEY: MISC_FEATURE
<222> LOCATION: (2)..(2)
<223> OTHER INFORMATION: Xaa is X4, being T, S, P, D or N
<220> FEATURE:
<221> NAME/KEY: MISC_FEATURE
<222> LOCATION: (3)..(3)
<223> OTHER INFORMATION: Xaa is X5, being any amino acid (A, R, D, N, C,
      G, Q, E, H, I, L, K, M, F, P, S, T, V, W or Y)
<220> FEATURE:
<221> NAME/KEY: MISC_FEATURE
<222> LOCATION: (5)..(5)
<223> OTHER INFORMATION: Xaa is X6, being Q, E, L, M, A, or W
<220> FEATURE:
<221> NAME/KEY: MISC_FEATURE
<222> LOCATION: (6)..(7)
<223> OTHER INFORMATION: Xaa are X7 and X8, being amino acid favorable
      to an alpha helix secondary structure, preferably A, R, D, N, C,
      G, Q, E, H, L, K, M, F, S, W or Y
<220> FEATURE:
<221> NAME/KEY: MISC_FEATURE
<222> LOCATION: (9)..(9)
<223> OTHER INFORMATION: Xaa is X9, being an amino acid favorable to an
      alpha helix secondary structure, preferably A, R, D, N, C, G, Q,
      E, H, L, K, M, F, S, W or Y
<220> FEATURE:
<221> NAME/KEY: MISC_FEATURE
<222> LOCATION: (10)..(10)
<223> OTHER INFORMATION: Xaa is X10, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (13)..(13)
<223> OTHER INFORMATION: Xaa is X11, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X12, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (17)..(17)
<223> OTHER INFORMATION: Xaa is X13, being missing or being selected
      from the group consisting of G, A and S
<220> FEATURE:
<221> NAME/KEY: MISC_FEATURE
<222> LOCATION: (18)..(18)
<223> OTHER INFORMATION: Xaa is X14, being missing or being any amino
      acid (A, R, D, N, C, G, Q, E, H, I, L, K, M, F, P, S, T, V, W or
      Y)
<220> FEATURE:
<221> NAME/KEY: MISC_FEATURE
<222> LOCATION: (19)..(19)
<223> OTHER INFORMATION: Xaa is X15, being A, T, V, I or R
<220> FEATURE:
<221> NAME/KEY: MISC_FEATURE
<222> LOCATION: (20)..(20)
<223> OTHER INFORMATION: Xaa is X16, being T or V
<220> FEATURE:
<221> NAME/KEY: MISC_FEATURE
<222> LOCATION: (21)..(21)
<223> OTHER INFORMATION: Xaa is X17, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (22)..(22)
<223> OTHER INFORMATION: Xaa is X18, being any non-positively charged
      amino acid (A, D, N, C, G, Q, E, H, I, L, M, F, P, S, T, V, W or
      Y)
<220> FEATURE:
<221> NAME/KEY: MISC_FEATURE
<222> LOCATION: (24)..(24)
<223> OTHER INFORMATION: Xaa is X19, being a hydrophobic amino acid,
      preferably A, C, V, P, L, I, M, F, W or Y
<220> FEATURE:
```

```
<221> NAME/KEY: MISC_FEATURE
<222> LOCATION: (25)..(25)
<223> OTHER INFORMATION: Xaa is X20, being missing or being any amino
      acid (A, R, D, N, C, G, Q, E, H, I, L, K, M, F, P, S, T, V, W or
      Y)

<400> SEQUENCE: 9

Xaa Xaa Xaa Lys Xaa Xaa Xaa Leu Xaa Xaa Arg Ile Xaa Gly Xaa Gly
1               5                   10                  15

Xaa Xaa Xaa Xaa Xaa Xaa Gly Xaa Xaa
            20                  25

<210> SEQ ID NO 10
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa are X1 and X2, being any amino acid (A, R,
      D, N, C, G, Q, E, H, I, L, K, M, F, P, S, T, V, W or Y)
<220> FEATURE:
<221> NAME/KEY: MISC_FEATURE
<222> LOCATION: (3)..(3)
<223> OTHER INFORMATION: Xaa is X3, being T, S, P, D or N
<220> FEATURE:
<221> NAME/KEY: MISC_FEATURE
<222> LOCATION: (4)..(5)
<223> OTHER INFORMATION: Xaa are X4 and X5, being an amino acid
      favorable to an alpha helix secondary structure, preferably A, R,
      D, N, C, G, Q, E, H, L, K, M, F, S, W or Y
<220> FEATURE:
<221> NAME/KEY: MISC_FEATURE
<222> LOCATION: (7)..(7)
<223> OTHER INFORMATION: Xaa is X6, being Q, E, L, M, A, or W
<220> FEATURE:
<221> NAME/KEY: MISC_FEATURE
<222> LOCATION: (8)..(9)
<223> OTHER INFORMATION: Xaa are X7 and X8, being an amino acid
      favorable to an alpha helix secondary structure, preferably A, R,
      D, N, C, G, Q, E, H, L, K, M, F, S, W or Y
<220> FEATURE:
<221> NAME/KEY: MISC_FEATURE
<222> LOCATION: (11)..(11)
<223> OTHER INFORMATION: Xaa is X9, being an amino acid favorable to an
      alpha helix secondary structure, preferably A, R, D, N, C, G, Q,
      E, H, L, K, M, F, S, W or Y
<220> FEATURE:
<221> NAME/KEY: MISC_FEATURE
<222> LOCATION: (12)..(12)
<223> OTHER INFORMATION: Xaa is X10, being any amino acid, (A, R, D, N,
      C, G, Q, E, H, I, L, K, M, F, P, S, T, V, W or Y)
<220> FEATURE:
<221> NAME/KEY: MISC_FEATURE
<222> LOCATION: (15)..(15)
<223> OTHER INFORMATION: Xaa is X11, being any amino acid, (A, R, D, N,
      C, G, Q, E, H, I, L, K, M, F, P, S, T, V, W or Y)
<220> FEATURE:
<221> NAME/KEY: MISC_FEATURE
<222> LOCATION: (17)..(17)
<223> OTHER INFORMATION: Xaa is X12, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (19)..(19)
<223> OTHER INFORMATION: Xaa is X13, being missing or being an amino
      acid selected from the group consisting of G, A and S
<220> FEATURE:
<221> NAME/KEY: MISC_FEATURE
<222> LOCATION: (20)..(20)
<223> OTHER INFORMATION: Xaa is X14, being missing or being any amino
      acid (A, R, D, N, C, G, Q, E, H, I, L, K, M, F, P, S, T, V, W or
      Y)
<220> FEATURE:
```

```
<221> NAME/KEY: MISC_FEATURE
<222> LOCATION: (21)..(21)
<223> OTHER INFORMATION: Xaa is X15, being A, T, V, I or R
<220> FEATURE:
<221> NAME/KEY: MISC_FEATURE
<222> LOCATION: (22)..(22)
<223> OTHER INFORMATION: Xaa is X16, being T or V
<220> FEATURE:
<221> NAME/KEY: MISC_FEATURE
<222> LOCATION: (23)..(23)
<223> OTHER INFORMATION: Xaa is X17, being any amino acid (A, R, D, N,
      C, G, Q, E, H, I, L, K, M, F, P, S, T, V, W or Y)
<220> FEATURE:
<221> NAME/KEY: MISC_FEATURE
<222> LOCATION: (24)..(24)
<223> OTHER INFORMATION: Xaa is X18, being any non-positively charged
      amino acid (A, D, N, C, G, Q, E, H, I, L, M, F, P, S, T, V, W or
      Y)
<220> FEATURE:
<221> NAME/KEY: MISC_FEATURE
<222> LOCATION: (26)..(26)
<223> OTHER INFORMATION: Xaa is X19, being a hydrophobic amino acid,
      preferably A, C, V, P, L, I, M, F, W or Y
<220> FEATURE:
<221> NAME/KEY: MISC_FEATURE
<222> LOCATION: (27)..(27)
<223> OTHER INFORMATION: Xaa is X20, being any amino acid (A, R, D, N,
      C, G, Q, E, H, I, L, K, M, F, P, S, T, V, W or Y)

<400> SEQUENCE: 10

Xaa Xaa Xaa Xaa Xaa Lys Xaa Xaa Xaa Leu Xaa Xaa Arg Ile Xaa Gly
1               5                   10                  15

Xaa Gly Xaa Xaa Xaa Xaa Xaa Xaa Gly Xaa Xaa
            20                  25

<210> SEQ ID NO 11
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is X3, being I, R or L
<220> FEATURE:
<221> NAME/KEY: MISC_FEATURE
<222> LOCATION: (2)..(2)
<223> OTHER INFORMATION: Xaa is X4, being T or M
<220> FEATURE:
<221> NAME/KEY: MISC_FEATURE
<222> LOCATION: (5)..(5)
<223> OTHER INFORMATION: Xaa is X6, being E or D
<220> FEATURE:
<221> NAME/KEY: MISC_FEATURE
<222> LOCATION: (6)..(6)
<223> OTHER INFORMATION: Xaa is X7, being R, A, I or E
<220> FEATURE:
<221> NAME/KEY: MISC_FEATURE
<222> LOCATION: (7)..(7)
<223> OTHER INFORMATION: Xaa is X8, being R, Q or E
<220> FEATURE:
<221> NAME/KEY: MISC_FEATURE
<222> LOCATION: (9)..(9)
<223> OTHER INFORMATION: Xaa is X9, being R or A
<220> FEATURE:
<221> NAME/KEY: MISC_FEATURE
<222> LOCATION: (13)..(13)
<223> OTHER INFORMATION: Xaa is X11, being R or E
<220> FEATURE:
<221> NAME/KEY: MISC_FEATURE
<222> LOCATION: (15)..(15)
<223> OTHER INFORMATION: Xaa is X12, being A or P
<220> FEATURE:
<221> NAME/KEY: MISC_FEATURE
<222> LOCATION: (17)..(17)
```

-continued

```
<223> OTHER INFORMATION: Xaa is X13, being missing or being an amino
      acid selected from the group consisting of G, A and S
<220> FEATURE:
<221> NAME/KEY: MISC_FEATURE
<222> LOCATION: (18)..(18)
<223> OTHER INFORMATION: Xaa is X14, being missing or S
<220> FEATURE:
<221> NAME/KEY: MISC_FEATURE
<222> LOCATION: (19)..(19)
<223> OTHER INFORMATION: Xaa is X15, being R or V
<220> FEATURE:
<221> NAME/KEY: MISC_FEATURE
<222> LOCATION: (20)..(20)
<223> OTHER INFORMATION: Xaa is X16, being T or V
<220> FEATURE:
<221> NAME/KEY: MISC_FEATURE
<222> LOCATION: (22)..(22)
<223> OTHER INFORMATION: Xaa is X18, being Y, N or D
<220> FEATURE:
<221> NAME/KEY: MISC_FEATURE
<222> LOCATION: (24)..(24)
<223> OTHER INFORMATION: Xaa is X19, being F, M, A or Q
<220> FEATURE:
<221> NAME/KEY: MISC_FEATURE
<222> LOCATION: (25)..(25)
<223> OTHER INFORMATION: Xaa is X20, being G, Q or N

<400> SEQUENCE: 11

Xaa Xaa Pro Lys Xaa Xaa Xaa Leu Xaa Arg Arg Ile Xaa Gly Xaa Gly
1               5                   10                  15

Xaa Xaa Xaa Xaa Leu Xaa Gly Xaa Xaa
            20                  25

<210> SEQ ID NO 12
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa is X4, being E or R
<220> FEATURE:
<221> NAME/KEY: MISC_FEATURE
<222> LOCATION: (17)..(17)
<223> OTHER INFORMATION: Xaa is X12, being A or P
<220> FEATURE:
<221> NAME/KEY: MISC_FEATURE
<222> LOCATION: (19)..(19)
<223> OTHER INFORMATION: Xaa is X13, being missing or being selected
      from the group consisting of G, A and S
<220> FEATURE:
<221> NAME/KEY: MISC_FEATURE
<222> LOCATION: (20)..(20)
<223> OTHER INFORMATION: Xaa is X14, being missing or S
<220> FEATURE:
<221> NAME/KEY: MISC_FEATURE
<222> LOCATION: (21)..(21)
<223> OTHER INFORMATION: Xaa is X15, being R or V
<220> FEATURE:
<221> NAME/KEY: MISC_FEATURE
<222> LOCATION: (22)..(22)
<223> OTHER INFORMATION: Xaa is X16, being T or V
<220> FEATURE:
<221> NAME/KEY: MISC_FEATURE
<222> LOCATION: (24)..(24)
<223> OTHER INFORMATION: Xaa is X18, being Y, N or D
<220> FEATURE:
<221> NAME/KEY: MISC_FEATURE
<222> LOCATION: (26)..(26)
<223> OTHER INFORMATION: Xaa is X19, being F, M, A or Q
<220> FEATURE:
<221> NAME/KEY: MISC_FEATURE
<222> LOCATION: (27)..(27)
<223> OTHER INFORMATION: Xaa is X20, being G, Q or N
```

```
<400> SEQUENCE: 12

Ala Ser Thr Xaa Arg Lys Trp Ala Glu Leu Ala Arg Arg Ile Arg Gly
1               5                   10                  15

Xaa Gly Xaa Xaa Xaa Xaa Leu Xaa Gly Xaa Xaa
            20                  25

<210> SEQ ID NO 13
<211> LENGTH: 24
<212> TYPE: PRT
<213> ORGANISM: artificial sequence
<220> FEATURE:
<223> OTHER INFORMATION: synthetic peptide

<400> SEQUENCE: 13

Ile Met Pro Lys Asp Ile Gln Leu Ala Arg Arg Ile Arg Gly Ala Gly
1               5                   10                  15

Gly Arg Thr Leu Tyr Gly Phe Gly
            20

<210> SEQ ID NO 14
<211> LENGTH: 25
<212> TYPE: PRT
<213> ORGANISM: artificial sequence
<220> FEATURE:
<223> OTHER INFORMATION: synthetic peptide

<400> SEQUENCE: 14

Ile Met Pro Lys Asp Ile Gln Leu Ala Arg Arg Ile Arg Gly Ala Gly
1               5                   10                  15

Ala Ser Arg Thr Leu Tyr Gly Phe Gly
            20                  25

<210> SEQ ID NO 15
<211> LENGTH: 24
<212> TYPE: PRT
<213> ORGANISM: artificial sequence
<220> FEATURE:
<223> OTHER INFORMATION: synthetic peptide

<400> SEQUENCE: 15

Ile Thr Pro Lys Glu Ala Gln Leu Ala Arg Arg Ile Arg Gly Ala Gly
1               5                   10                  15

Gly Arg Thr Leu Asn Gly Phe Gly
            20

<210> SEQ ID NO 16
<211> LENGTH: 25
<212> TYPE: PRT
<213> ORGANISM: artificial sequence
<220> FEATURE:
<223> OTHER INFORMATION: synthetic peptide

<400> SEQUENCE: 16

Ile Thr Pro Lys Glu Ala Gln Leu Ala Arg Arg Ile Arg Gly Ala Gly
1               5                   10                  15

Ala Ser Arg Thr Leu Asn Gly Phe Gly
            20                  25

<210> SEQ ID NO 17
<211> LENGTH: 24
<212> TYPE: PRT
<213> ORGANISM: artificial sequence
<220> FEATURE:
```

<223> OTHER INFORMATION: synthetic peptide

<400> SEQUENCE: 17

Leu Thr Pro Lys Glu Ala Glu Leu Ala Arg Arg Ile Arg Gly Ala Gly
1               5                   10                  15

Gly Arg Thr Leu Asn Gly Phe Gly
            20

<210> SEQ ID NO 18
<211> LENGTH: 25
<212> TYPE: PRT
<213> ORGANISM: artificial sequence
<220> FEATURE:
<223> OTHER INFORMATION: synthetic peptide

<400> SEQUENCE: 18

Leu Thr Pro Lys Glu Ala Glu Leu Ala Arg Arg Ile Arg Gly Ala Gly
1               5                   10                  15

Ala Ser Arg Thr Leu Asn Gly Phe Gly
            20                  25

<210> SEQ ID NO 19
<211> LENGTH: 25
<212> TYPE: PRT
<213> ORGANISM: artificial sequence
<220> FEATURE:
<223> OTHER INFORMATION: synthetic peptide

<400> SEQUENCE: 19

Ile Thr Pro Lys Glu Ala Gln Leu Ala Arg Arg Ile Glu Gly Ala Gly
1               5                   10                  15

Ala Ser Val Thr Leu Asn Gly Phe Gly
            20                  25

<210> SEQ ID NO 20
<211> LENGTH: 25
<212> TYPE: PRT
<213> ORGANISM: artificial sequence
<220> FEATURE:
<223> OTHER INFORMATION: synthetic peptide

<400> SEQUENCE: 20

Leu Thr Pro Lys Glu Ala Glu Leu Ala Arg Arg Ile Glu Gly Ala Gly
1               5                   10                  15

Ala Ser Val Thr Leu Asn Gly Phe Gly
            20                  25

<210> SEQ ID NO 21
<211> LENGTH: 25
<212> TYPE: PRT
<213> ORGANISM: artificial sequence
<220> FEATURE:
<223> OTHER INFORMATION: synthetic peptide

<400> SEQUENCE: 21

Ile Thr Pro Lys Glu Glu Gln Leu Arg Arg Arg Ile Glu Gly Ala Gly
1               5                   10                  15

Ala Ser Val Thr Leu Asn Gly Phe Gly
            20                  25

<210> SEQ ID NO 22
<211> LENGTH: 24
<212> TYPE: PRT
<213> ORGANISM: artificial sequence

```
<220> FEATURE:
<223> OTHER INFORMATION: synthetic peptide

<400> SEQUENCE: 22

Ile Thr Pro Lys Glu Ala Gln Leu Ala Arg Arg Ile Arg Gly Ala Gly
1               5                   10                  15

Gly Val Thr Leu Asn Gly Phe Gly
            20

<210> SEQ ID NO 23
<211> LENGTH: 24
<212> TYPE: PRT
<213> ORGANISM: artificial sequence
<220> FEATURE:
<223> OTHER INFORMATION: synthetic peptide

<400> SEQUENCE: 23

Leu Thr Pro Lys Glu Ala Glu Leu Ala Arg Arg Ile Arg Gly Ala Gly
1               5                   10                  15

Gly Val Thr Leu Asn Gly Phe Gly
            20

<210> SEQ ID NO 24
<211> LENGTH: 23
<212> TYPE: PRT
<213> ORGANISM: artificial sequence
<220> FEATURE:
<223> OTHER INFORMATION: synthetic peptide

<400> SEQUENCE: 24

Leu Thr Pro Lys Glu Ala Glu Leu Ala Arg Arg Ile Arg Gly Ala Gly
1               5                   10                  15

Arg Thr Leu Asn Gly Phe Gly
            20

<210> SEQ ID NO 25
<211> LENGTH: 24
<212> TYPE: PRT
<213> ORGANISM: artificial sequence
<220> FEATURE:
<223> OTHER INFORMATION: synthetic peptide

<400> SEQUENCE: 25

Leu Thr Pro Lys Glu Ala Glu Leu Ala Arg Arg Ile Arg Gly Ala Gly
1               5                   10                  15

Gly Arg Thr Leu Asn Gly Phe Gly
            20

<210> SEQ ID NO 26
<211> LENGTH: 25
<212> TYPE: PRT
<213> ORGANISM: artificial sequence
<220> FEATURE:
<223> OTHER INFORMATION: synthetic peptide

<400> SEQUENCE: 26

Leu Thr Pro Lys Glu Ala Glu Leu Ala Arg Arg Ile Arg Gly Ala Gly
1               5                   10                  15

Ala Ser Arg Thr Leu Asn Gly Phe Gly
            20                  25

<210> SEQ ID NO 27
<211> LENGTH: 24
<212> TYPE: PRT
```

```
<213> ORGANISM: artificial sequence
<220> FEATURE:
<223> OTHER INFORMATION: synthetic peptide

<400> SEQUENCE: 27

Arg Thr Pro Lys Glu Arg Arg Leu Ala Arg Arg Ile Arg Gly Ala Gly
1               5                   10                  15

Gly Arg Thr Leu Asn Gly Phe Gly
            20

<210> SEQ ID NO 28
<211> LENGTH: 24
<212> TYPE: PRT
<213> ORGANISM: artificial
<220> FEATURE:
<223> OTHER INFORMATION: synthetic peptide

<400> SEQUENCE: 28

Arg Thr Pro Lys Glu Ala Arg Leu Ala Arg Arg Ile Arg Gly Ala Gly
1               5                   10                  15

Gly Arg Thr Leu Asn Gly Phe Gly
            20

<210> SEQ ID NO 29
<211> LENGTH: 24
<212> TYPE: PRT
<213> ORGANISM: artificial sequence
<220> FEATURE:
<223> OTHER INFORMATION: synthetic peptide

<400> SEQUENCE: 29

Leu Thr Pro Lys Glu Ala Glu Leu Ala Arg Arg Ile Arg Gly Ala Gly
1               5                   10                  15

Gly Val Thr Tyr Asp Gly Phe Gly
            20

<210> SEQ ID NO 30
<211> LENGTH: 24
<212> TYPE: PRT
<213> ORGANISM: artificial sequence
<220> FEATURE:
<223> OTHER INFORMATION: synthetic peptide

<400> SEQUENCE: 30

Leu Thr Pro Lys Glu Ala Glu Leu Ala Arg Arg Ile Arg Gly Ala Gly
1               5                   10                  15

Gly Val Thr Leu Asn Gly Ala Asn
            20

<210> SEQ ID NO 31
<211> LENGTH: 25
<212> TYPE: PRT
<213> ORGANISM: artificial sequence
<220> FEATURE:
<223> OTHER INFORMATION: synthetic peptide

<400> SEQUENCE: 31

Ser Thr Glu Arg Lys Trp Ala Glu Leu Ala Arg Arg Ile Arg Gly Ala
1               5                   10                  15

Gly Gly Val Thr Leu Asn Gly Phe Gly
            20                  25

<210> SEQ ID NO 32
<211> LENGTH: 26
```

```
<212> TYPE: PRT
<213> ORGANISM: artificial sequence
<220> FEATURE:
<223> OTHER INFORMATION: synthetic peptide

<400> SEQUENCE: 32

Ala Ser Thr Glu Arg Lys Trp Ala Glu Leu Ala Arg Arg Ile Arg Gly
1               5                   10                  15

Ala Gly Gly Val Thr Leu Asn Gly Phe Gly
            20                  25

<210> SEQ ID NO 33
<211> LENGTH: 26
<212> TYPE: PRT
<213> ORGANISM: artificial sequence
<220> FEATURE:
<223> OTHER INFORMATION: synthetic peptide

<400> SEQUENCE: 33

Ala Ser Thr Arg Arg Lys Trp Ala Glu Leu Ala Arg Arg Ile Arg Gly
1               5                   10                  15

Ala Gly Gly Val Thr Leu Asn Gly Phe Gly
            20                  25

<210> SEQ ID NO 34
<211> LENGTH: 9
<212> TYPE: PRT
<213> ORGANISM: Artificial sequence
<220> FEATURE:
<223> OTHER INFORMATION: synthetic peptide

<400> SEQUENCE: 34

Arg Lys Lys Arg Arg Gln Arg Arg Arg
1               5

<210> SEQ ID NO 35
<211> LENGTH: 16
<212> TYPE: PRT
<213> ORGANISM: artificial sequence
<220> FEATURE:
<223> OTHER INFORMATION: synthetic peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 9
<212> TYPE: PRT
<213> ORGANISM: artificial sequence
<220> FEATURE:
<223> OTHER INFORMATION: synthetic peptide

<400> SEQUENCE: 36

Arg Arg Arg Arg Arg Arg Arg Arg Arg
1               5

<210> SEQ ID NO 37
<211> LENGTH: 15
<212> TYPE: PRT
<213> ORGANISM: artificial sequence
<220> FEATURE:
<223> OTHER INFORMATION: synthetic peptide

<400> SEQUENCE: 37

Arg Arg Pro Arg Arg Pro Arg Arg Pro Arg Arg Pro Arg Arg Pro
```

<210> SEQ ID NO 38
<211> LENGTH: 29
<212> TYPE: PRT
<213> ORGANISM: artificial sequence
<220> FEATURE:
<223> OTHER INFORMATION: synthetic peptide

<400> SEQUENCE: 38

Gly Ala Met Gly Thr Ile Met Pro Lys Asp Ile Gln Leu Ala Arg Arg
1               5                   10                  15

Ile Arg Gly Ala Gly Gly Arg Thr Leu Tyr Gly Phe Gly
            20                  25

<210> SEQ ID NO 39
<211> LENGTH: 30
<212> TYPE: PRT
<213> ORGANISM: artificial sequence
<220> FEATURE:
<223> OTHER INFORMATION: synthetic peptide

<400> SEQUENCE: 39

Gly Ala Met Gly Thr Ile Met Pro Lys Asp Ile Gln Leu Ala Arg Arg
1               5                   10                  15

Ile Arg Gly Ala Gly Ala Ser Arg Thr Leu Tyr Gly Phe Gly
            20                  25                  30

<210> SEQ ID NO 40
<211> LENGTH: 29
<212> TYPE: PRT
<213> ORGANISM: artificial sequence
<220> FEATURE:
<223> OTHER INFORMATION: synthetic peptide

<400> SEQUENCE: 40

Gly Ala Met Gly Thr Ile Thr Pro Lys Glu Ala Gln Leu Ala Arg Arg
1               5                   10                  15

Ile Arg Gly Ala Gly Gly Arg Thr Leu Asn Gly Phe Gly
            20                  25

<210> SEQ ID NO 41
<211> LENGTH: 30
<212> TYPE: PRT
<213> ORGANISM: artificial sequence
<220> FEATURE:
<223> OTHER INFORMATION: synthetic peptide

<400> SEQUENCE: 41

Gly Ala Met Gly Thr Ile Thr Pro Lys Glu Ala Gln Leu Ala Arg Arg
1               5                   10                  15

Ile Arg Gly Ala Gly Ala Ser Arg Thr Leu Asn Gly Phe Gly
            20                  25                  30

<210> SEQ ID NO 42
<211> LENGTH: 29
<212> TYPE: PRT
<213> ORGANISM: artificial sequence
<220> FEATURE:
<223> OTHER INFORMATION: synthetic peptide

<400> SEQUENCE: 42

Gly Ala Met Gly Thr Leu Thr Pro Lys Glu Ala Glu Leu Ala Arg Arg
1               5                   10                  15

Ile Arg Gly Ala Gly Gly Arg Thr Leu Asn Gly Phe Gly
            20                  25

<210> SEQ ID NO 43
<211> LENGTH: 30
<212> TYPE: PRT
<213> ORGANISM: artificial
<220> FEATURE:
<223> OTHER INFORMATION: synthetic peptide

<400> SEQUENCE: 43

Gly Ala Met Gly Thr Leu Thr Pro Lys Glu Ala Glu Leu Ala Arg Arg
1               5                   10                  15

Ile Arg Gly Ala Gly Ala Ser Arg Thr Leu Asn Gly Phe Gly
            20                  25                  30

<210> SEQ ID NO 44
<211> LENGTH: 30
<212> TYPE: PRT
<213> ORGANISM: artificial sequence
<220> FEATURE:
<223> OTHER INFORMATION: synthetic peptide

<400> SEQUENCE: 44

Gly Ala Met Gly Thr Ile Thr Pro Lys Glu Ala Gln Leu Ala Arg Arg
1               5                   10                  15

Ile Glu Gly Ala Gly Ala Ser Val Thr Leu Asn Gly Phe Gly
            20                  25                  30

<210> SEQ ID NO 45
<211> LENGTH: 30
<212> TYPE: PRT
<213> ORGANISM: artificial sequence
<220> FEATURE:
<223> OTHER INFORMATION: synthetic peptide

<400> SEQUENCE: 45

Gly Ala Met Gly Thr Leu Thr Pro Lys Glu Ala Glu Leu Ala Arg Arg
1               5                   10                  15

Ile Glu Gly Ala Gly Ala Ser Val Thr Leu Asn Gly Phe Gly
            20                  25                  30

<210> SEQ ID NO 46
<211> LENGTH: 30
<212> TYPE: PRT
<213> ORGANISM: artificial sequence
<220> FEATURE:
<223> OTHER INFORMATION: synthetic peptide

<400> SEQUENCE: 46

Gly Ala Met Gly Thr Ile Thr Pro Lys Glu Glu Gln Leu Arg Arg Arg
1               5                   10                  15

Ile Glu Gly Ala Gly Ala Ser Val Thr Leu Asn Gly Phe Gly
            20                  25                  30

<210> SEQ ID NO 47
<211> LENGTH: 29
<212> TYPE: PRT
<213> ORGANISM: artificial sequence
<220> FEATURE:
<223> OTHER INFORMATION: synthetic peptide

<400> SEQUENCE: 47

Gly Ala Met Gly Thr Ile Thr Pro Lys Glu Ala Gln Leu Ala Arg Arg
1               5                   10                  15

Ile Arg Gly Ala Gly Gly Val Thr Leu Asn Gly Phe Gly
            20                  25

<210> SEQ ID NO 48
<211> LENGTH: 29
<212> TYPE: PRT
<213> ORGANISM: artificial sequence
<220> FEATURE:
<223> OTHER INFORMATION: synthetic peptide

<400> SEQUENCE: 48

Gly Ala Met Gly Thr Leu Thr Pro Lys Glu Ala Glu Leu Ala Arg Arg
1               5                   10                  15

Ile Arg Gly Ala Gly Gly Val Thr Leu Asn Gly Phe Gly
            20                  25

<210> SEQ ID NO 49
<211> LENGTH: 28
<212> TYPE: PRT
<213> ORGANISM: artificial sequence
<220> FEATURE:
<223> OTHER INFORMATION: synthetic peptide

<400> SEQUENCE: 49

Gly Ala Met Gly Thr Leu Thr Pro Lys Glu Ala Glu Leu Ala Arg Arg
1               5                   10                  15

Ile Arg Gly Ala Gly Arg Thr Leu Asn Gly Phe Gly
            20                  25

<210> SEQ ID NO 50
<211> LENGTH: 46
<212> TYPE: PRT
<213> ORGANISM: artificial sequence
<220> FEATURE:
<223> OTHER INFORMATION: synthetic peptide

<400> SEQUENCE: 50

Arg Arg Pro Arg Arg Pro Arg Pro Arg Arg Pro Arg Arg Pro Gly
1               5                   10                  15

Ala Met Gly Thr Ile Thr Pro Lys Glu Ala Gln Leu Ala Arg Arg Ile
            20                  25                  30

Arg Gly Ala Gly Gly Val Thr Leu Asn Gly Phe Gly Cys Ala
        35                  40                  45

<210> SEQ ID NO 51
<211> LENGTH: 30
<212> TYPE: PRT
<213> ORGANISM: artificial sequence
<220> FEATURE:
<223> OTHER INFORMATION: synthetic peptide

<400> SEQUENCE: 51

Gly Ala Met Gly Thr Leu Thr Pro Lys Glu Ala Glu Leu Ala Arg Arg
1               5                   10                  15

Ile Arg Gly Ala Gly Ala Ser Arg Thr Leu Asn Gly Phe Gly
            20                  25                  30

<210> SEQ ID NO 52
<211> LENGTH: 39
<212> TYPE: PRT
<213> ORGANISM: artificial sequence
<220> FEATURE:
<223> OTHER INFORMATION: synthetic peptide -continued

```
<400> SEQUENCE: 52

Gly Ala Met Gly Leu Thr Ala Ala Glu His Ala Lys Arg Ser Thr Leu
1               5                   10                  15

Thr Pro Lys Glu Ala Gln Leu Ala Arg Arg Ile Arg Gly Ala Gly Gly
            20                  25                  30

Val Thr Leu Asn Gly Phe Gly
            35

<210> SEQ ID NO 53
<211> LENGTH: 35
<212> TYPE: PRT
<213> ORGANISM: artificial sequence
<220> FEATURE:
<223> OTHER INFORMATION: synthetic peptide

<400> SEQUENCE: 53

Leu Thr Ala Ala Glu His Ala Lys Arg Ser Thr Leu Thr Pro Lys Glu
1               5                   10                  15

Ala Glu Leu Ala Arg Arg Ile Arg Gly Ala Gly Gly Val Thr Leu Asn
            20                  25                  30

Gly Phe Gly
        35

<210> SEQ ID NO 54
<211> LENGTH: 36
<212> TYPE: PRT
<213> ORGANISM: artificial sequence
<220> FEATURE:
<223> OTHER INFORMATION: synthetic peptide

<400> SEQUENCE: 54

Leu Thr Ala Ala Glu His Ala Lys Arg Ser Thr Leu Thr Pro Lys Glu
1               5                   10                  15

Ala Gln Leu Ala Arg Arg Ile Glu Gly Ala Gly Ala Ser Val Thr Leu
            20                  25                  30

Asn Gly Phe Gly
        35

<210> SEQ ID NO 55
<211> LENGTH: 36
<212> TYPE: PRT
<213> ORGANISM: artificial sequence
<220> FEATURE:
<223> OTHER INFORMATION: synthetic peptide

<400> SEQUENCE: 55

Leu Thr Ala Ala Glu His Ala Lys Arg Ser Thr Leu Thr Pro Lys Glu
1               5                   10                  15

Ala Glu Leu Ala Arg Arg Ile Glu Gly Ala Gly Ala Ser Val Thr Leu
            20                  25                  30

Asn Gly Phe Gly
        35

<210> SEQ ID NO 56
<211> LENGTH: 29
<212> TYPE: PRT
<213> ORGANISM: artificial sequence
<220> FEATURE:
<223> OTHER INFORMATION: synthetic peptide

<400> SEQUENCE: 56

Gly Ala Met Gly Thr Arg Thr Pro Lys Glu Arg Arg Leu Ala Arg Arg
```

```
                1               5                   10                  15
Ile Arg Gly Ala Gly Gly Arg Thr Leu Asn Gly Phe Gly
            20                  25
```

<210> SEQ ID NO 57
<211> LENGTH: 29
<212> TYPE: PRT
<213> ORGANISM: artificial sequence
<220> FEATURE:
<223> OTHER INFORMATION: synthetic peptide

<400> SEQUENCE: 57

```
Gly Ala Met Gly Thr Arg Thr Pro Lys Glu Ala Arg Leu Ala Arg Arg
1               5                   10                  15

Ile Arg Gly Ala Gly Gly Arg Thr Leu Asn Gly Phe Gly
            20                  25
```

<210> SEQ ID NO 58
<211> LENGTH: 39
<212> TYPE: PRT
<213> ORGANISM: artificial sequence
<220> FEATURE:
<223> OTHER INFORMATION: synthetic peptide

<400> SEQUENCE: 58

```
Gly Arg Lys Lys Arg Arg Gln Arg Arg Gly Ala Met Gly Thr Ile
1               5                   10                  15

Thr Pro Lys Glu Ala Gln Leu Ala Arg Arg Ile Arg Gly Ala Gly Gly
            20                  25                  30

Val Thr Leu Asn Gly Phe Gly
            35
```

<210> SEQ ID NO 59
<211> LENGTH: 44
<212> TYPE: PRT
<213> ORGANISM: artificial sequence
<220> FEATURE:
<223> OTHER INFORMATION: synthetic peptide

<400> SEQUENCE: 59

```
Arg Arg Pro Arg Arg Pro Arg Arg Pro Arg Arg Pro Arg Arg Pro Gly
1               5                   10                  15

Ala Met Gly Thr Ile Thr Pro Lys Glu Ala Gln Leu Ala Arg Arg Ile
            20                  25                  30

Arg Gly Ala Gly Gly Val Thr Leu Asn Gly Phe Gly
            35                  40
```

<210> SEQ ID NO 60
<211> LENGTH: 37
<212> TYPE: PRT
<213> ORGANISM: artificial sequence
<220> FEATURE:
<223> OTHER INFORMATION: synthetic peptide

<400> SEQUENCE: 60

```
Arg Arg Pro Arg Arg Pro Arg Arg Pro Arg Arg Pro Arg Arg Pro Gly
1               5                   10                  15

Ala Met Gly Thr Ile Met Pro Lys Asp Ile Gln Leu Ala Arg Arg Ile
            20                  25                  30

Arg Gly Gly Cys Ala
            35
```

```
<210> SEQ ID NO 61
<211> LENGTH: 29
<212> TYPE: PRT
<213> ORGANISM: artificial sequence
<220> FEATURE:
<223> OTHER INFORMATION: synthetic peptide

<400> SEQUENCE: 61

Gly Ala Met Gly Thr Leu Thr Pro Lys Glu Ala Glu Leu Ala Arg Arg
1               5                   10                  15

Ile Arg Gly Ala Gly Gly Val Thr Tyr Asp Gly Phe Gly
            20                  25

<210> SEQ ID NO 62
<211> LENGTH: 33
<212> TYPE: PRT
<213> ORGANISM: artificial sequence
<220> FEATURE:
<223> OTHER INFORMATION: synthetic peptide

<400> SEQUENCE: 62

Gly Ala Met Gly Thr Leu Thr Pro Lys Glu Ala Glu Leu Ala Arg Arg
1               5                   10                  15

Ile Arg Gly Ala Gly Gly Val Thr Leu Asn Gly Phe Gly Ala Ser Thr
            20                  25                  30

Gly

<210> SEQ ID NO 63
<211> LENGTH: 34
<212> TYPE: PRT
<213> ORGANISM: artificial sequence
<220> FEATURE:
<223> OTHER INFORMATION: synthetic peptide

<400> SEQUENCE: 63

Gly Ala Met Gly Thr Leu Thr Pro Lys Glu Ala Glu Leu Ala Arg Arg
1               5                   10                  15

Ile Arg Gly Ala Gly Gly Val Thr Leu Asn Gly Ala Asn Phe Val Ser
            20                  25                  30

Thr Gly

<210> SEQ ID NO 64
<211> LENGTH: 40
<212> TYPE: PRT
<213> ORGANISM: artificial sequence
<220> FEATURE:
<223> OTHER INFORMATION: synthetic peptide

<400> SEQUENCE: 64

Gly Ala Met Gly Arg Val Pro Pro Ala Val Arg Lys Leu Gly Asn Ser
1               5                   10                  15

Thr Glu Arg Lys Trp Ala Glu Leu Ala Arg Arg Ile Arg Gly Ala Gly
            20                  25                  30

Gly Val Thr Leu Asn Gly Phe Gly
            35                  40

<210> SEQ ID NO 65
<211> LENGTH: 41
<212> TYPE: PRT
<213> ORGANISM: artificial sequence
<220> FEATURE:
<223> OTHER INFORMATION: synthetic peptide

<400> SEQUENCE: 65
```

```
Gly Ala Met Gly Arg Val Pro Pro Ala Val Arg Lys Leu Gly Asn Ala
1               5                   10                  15

Ser Thr Glu Arg Lys Trp Ala Glu Leu Ala Arg Arg Ile Arg Gly Ala
            20                  25                  30

Gly Gly Val Thr Leu Asn Gly Phe Gly
        35                  40

<210> SEQ ID NO 66
<211> LENGTH: 44
<212> TYPE: PRT
<213> ORGANISM: artificial sequence
<220> FEATURE:
<223> OTHER INFORMATION: synthetic peptide

<400> SEQUENCE: 66

Arg Arg Pro Arg Arg Pro Arg Arg Pro Arg Arg Pro Arg Arg Pro Ala
1               5                   10                  15

Ser Thr Glu Arg Lys Trp Ala Glu Leu Ala Arg Arg Ile Arg Gly Ala
            20                  25                  30

Gly Gly Val Thr Leu Asn Gly Phe Gly Gly Cys Ala
        35                  40

<210> SEQ ID NO 67
<211> LENGTH: 41
<212> TYPE: PRT
<213> ORGANISM: artificial sequence
<220> FEATURE:
<223> OTHER INFORMATION: synthetic peptide

<400> SEQUENCE: 67

Arg Arg Pro Arg Arg Pro Arg Arg Pro Arg Arg Pro Arg Arg Pro Ala
1               5                   10                  15

Ser Thr Glu Arg Lys Trp Ala Glu Leu Ala Arg Arg Ile Arg Gly Ala
            20                  25                  30

Gly Gly Val Thr Leu Asn Gly Phe Gly
        35                  40

<210> SEQ ID NO 68
<211> LENGTH: 26
<212> TYPE: PRT
<213> ORGANISM: artificial sequence
<220> FEATURE:
<223> OTHER INFORMATION: synthetic peptide

<400> SEQUENCE: 68

Ala Ser Thr Glu Arg Lys Trp Ala Glu Ala Ala Arg Ala Arg Gly
1               5                   10                  15

Ala Gly Gly Val Thr Leu Asn Gly Ala Gly
            20                  25

<210> SEQ ID NO 69
<211> LENGTH: 44
<212> TYPE: PRT
<213> ORGANISM: artificial sequence
<220> FEATURE:
<223> OTHER INFORMATION: synthetic peptide

<400> SEQUENCE: 69

Arg Arg Pro Arg Arg Pro Arg Arg Pro Arg Arg Pro Arg Arg Pro Ala
1               5                   10                  15

Ser Thr Glu Arg Lys Trp Ala Glu Ala Ala Arg Arg Ala Arg Gly Ala
            20                  25                  30
```

```
Gly Gly Val Thr Leu Asn Gly Ala Gly Gly Cys Ala
        35                  40

<210> SEQ ID NO 70
<211> LENGTH: 19
<212> TYPE: PRT
<213> ORGANISM: artificial sequence
<220> FEATURE:
<223> OTHER INFORMATION: synthetic peptide

<400> SEQUENCE: 70

Gly Ala Met Gly Thr Ile Met Pro Lys Asp Ile Gln Leu Ala Arg Arg
1               5                   10                  15

Ile Arg Gly

<210> SEQ ID NO 71
<211> LENGTH: 19
<212> TYPE: PRT
<213> ORGANISM: artificial sequence
<220> FEATURE:
<223> OTHER INFORMATION: synthetic peptide

<400> SEQUENCE: 71

Gly Ala Met Gly Thr Ile Thr Pro Lys Glu Ala Gln Leu Ala Arg Arg
1               5                   10                  15

Ile Arg Gly

<210> SEQ ID NO 72
<211> LENGTH: 19
<212> TYPE: PRT
<213> ORGANISM: artificial sequence
<220> FEATURE:
<223> OTHER INFORMATION: synthetic peptide

<400> SEQUENCE: 72

Gly Ala Met Gly Thr Leu Thr Pro Lys Glu Ala Glu Leu Ala Arg Arg
1               5                   10                  15

Ile Arg Gly

<210> SEQ ID NO 73
<211> LENGTH: 27
<212> TYPE: PRT
<213> ORGANISM: artificial sequence
<220> FEATURE:
<223> OTHER INFORMATION: synthetic peptide

<400> SEQUENCE: 73

Gly Ala Met Gly Thr Leu Thr Pro Lys Glu Ala Glu Leu Ala Arg Arg
1               5                   10                  15

Ile Arg Gly Ala Arg Thr Leu Asn Gly Phe Gly
            20                  25

<210> SEQ ID NO 74
<211> LENGTH: 31
<212> TYPE: PRT
<213> ORGANISM: artificial sequence
<220> FEATURE:
<223> OTHER INFORMATION: synthetic peptide

<400> SEQUENCE: 74

Gly Ala Met Gly Thr Leu Thr Pro Lys Glu Ala Glu Leu Ala Arg Arg
1               5                   10                  15

Ile Arg Gly Ala Gly Ala Ser Gly Arg Thr Leu Asn Gly Phe Gly
```

-continued

```
                20                  25                  30

<210> SEQ ID NO 75
<211> LENGTH: 26
<212> TYPE: PRT
<213> ORGANISM: artificial sequence
<220> FEATURE:
<223> OTHER INFORMATION: synthetic peptide

<400> SEQUENCE: 75

Ala Ser Thr Glu Glu Lys Trp Ala Arg Leu Ala Arg Arg Ile Arg Gly
1               5                   10                  15

Ala Gly Gly Val Thr Leu Asn Gly Phe Gly
            20                  25

<210> SEQ ID NO 76
<211> LENGTH: 26
<212> TYPE: PRT
<213> ORGANISM: artificial sequence
<220> FEATURE:
<223> OTHER INFORMATION: synthetic peptide

<400> SEQUENCE: 76

Ala Ser Thr Glu Arg Lys Trp Ala Glu Leu Ala Arg Arg Ile Arg Gly
1               5                   10                  15

Ala Gly Gly Val Thr Leu Asp Gly Phe Gly
            20                  25

<210> SEQ ID NO 77
<211> LENGTH: 26
<212> TYPE: PRT
<213> ORGANISM: artificial sequence
<220> FEATURE:
<223> OTHER INFORMATION: synthetic peptide

<400> SEQUENCE: 77

Ala Ser Thr Glu Arg Lys Trp Ala Glu Leu Ala Arg Arg Ile Arg Gly
1               5                   10                  15

Ala Gly Gly Arg Thr Leu Asn Gly Phe Gly
            20                  25

<210> SEQ ID NO 78
<211> LENGTH: 26
<212> TYPE: PRT
<213> ORGANISM: artificial sequence
<220> FEATURE:
<223> OTHER INFORMATION: synthetic peptide

<400> SEQUENCE: 78

Ala Ser Thr Glu Arg Lys Trp Ala Glu Leu Ala Arg Arg Ile Arg Gly
1               5                   10                  15

Ala Gly Gly Ala Thr Leu Asn Gly Phe Gly
            20                  25

<210> SEQ ID NO 79
<211> LENGTH: 26
<212> TYPE: PRT
<213> ORGANISM: artificial sequence
<220> FEATURE:
<223> OTHER INFORMATION: synthetic peptide

<400> SEQUENCE: 79

Ala Ser Thr Glu Arg Lys Trp Ala Glu Leu Ala Arg Arg Ile Ala Gly
1               5                   10                  15
```

Ala Gly Gly Val Thr Leu Asn Gly Phe Gly
            20                  25

<210> SEQ ID NO 80
<211> LENGTH: 26
<212> TYPE: PRT
<213> ORGANISM: artificial sequence
<220> FEATURE:
<223> OTHER INFORMATION: synthetic peptide

<400> SEQUENCE: 80

Ala Ser Thr Glu Glu Lys Trp Ala Arg Leu Ala Arg Arg Ile Ala Gly
1               5                   10                  15

Ala Gly Gly Val Thr Leu Asp Gly Phe Gly
            20                  25

<210> SEQ ID NO 81
<211> LENGTH: 41
<212> TYPE: PRT
<213> ORGANISM: artificial sequence
<220> FEATURE:
<223> OTHER INFORMATION: synthetic peptide

<400> SEQUENCE: 81

Arg Arg Pro Arg Arg Pro Arg Arg Pro Arg Arg Pro Arg Arg Pro Ala
1               5                   10                  15

Ser Thr Glu Glu Lys Trp Ala Arg Leu Ala Arg Arg Ile Ala Gly Ala
            20                  25                  30

Gly Gly Val Thr Leu Asp Gly Phe Gly
        35                  40

<210> SEQ ID NO 82
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (4)..(5)
<223> OTHER INFORMATION: Xaa is consecutively X4 and X5 and is E or R
<220> FEATURE:
<221> NAME/KEY: MISC_FEATURE
<222> LOCATION: (12)..(12)
<223> OTHER INFORMATION: Xaa is X8 being E or R
<220> FEATURE:
<221> NAME/KEY: MISC_FEATURE
<222> LOCATION: (15)..(15)
<223> OTHER INFORMATION: Xaa is X11 being R or A
<220> FEATURE:
<221> NAME/KEY: MISC_FEATURE
<222> LOCATION: (17)..(17)
<223> OTHER INFORMATION: Xaa is X12 being A or P
<220> FEATURE:
<221> NAME/KEY: MISC_FEATURE
<222> LOCATION: (19)..(19)
<223> OTHER INFORMATION: Xaa is X13 being missing or being an amino acid
      selected from the group consisting of G, A and S
<220> FEATURE:
<221> NAME/KEY: MISC_FEATURE
<222> LOCATION: (20)..(20)
<223> OTHER INFORMATION: Xaa is X14 being missing or S
<220> FEATURE:
<221> NAME/KEY: MISC_FEATURE
<222> LOCATION: (21)..(21)
<223> OTHER INFORMATION: Xaa is X15 being R, V or A
<220> FEATURE:
<221> NAME/KEY: MISC_FEATURE
<222> LOCATION: (22)..(22)
<223> OTHER INFORMATION: Xaa is X16 being T or V
<220> FEATURE:

```
<221> NAME/KEY: MISC_FEATURE
<222> LOCATION: (24)..(24)
<223> OTHER INFORMATION: Xaa is X18 being  Y, N or D
<220> FEATURE:
<221> NAME/KEY: MISC_FEATURE
<222> LOCATION: (26)..(26)
<223> OTHER INFORMATION: Xaa is X19 being  F or M
<220> FEATURE:
<221> NAME/KEY: MISC_FEATURE
<222> LOCATION: (27)..(27)
<223> OTHER INFORMATION: Xaa is X20 being G, Q or N

<400> SEQUENCE: 82

Ala Ser Thr Xaa Xaa Lys Trp Ala Glu Leu Ala Xaa Arg Ile Xaa Gly
1               5                   10                  15

Xaa Gly Xaa Xaa Xaa Xaa Leu Xaa Gly Xaa Xaa
            20                  25
```

UNITED STATES PATENT AND TRADEMARK OFFICE
CERTIFICATE OF CORRECTION

PATENT NO. : 9,526,757 B2  
APPLICATION NO. : 14/358875  
DATED : December 27, 2016  
INVENTOR(S) : Francoise Ochsenbein et al.

Page 1 of 1

It is certified that error appears in the above-identified patent and that said Letters Patent is hereby corrected as shown below:

In the Specification

Column 19,  
Line 47, "of 8 an" should read --of 8 µM, an--.  
Line 48, "180 nM 40 nM" should read --180nM ± 40nM--.

Column 21,  
Line 65, "0.5 or 0.16 and" should read --0.5 µM or 0.16 µM, and--.

Column 23,  
Line 6, "(200 The cycle" should read --(200 µM). The cycle--.

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*